United States Patent
Janow

(10) Patent No.: US 9,907,331 B2
(45) Date of Patent: *Mar. 6, 2018

(54) RICE PROTEIN SUPPLEMENT AND METHODS OF USE THEREOF

(71) Applicant: AXIOM FOODS, INC., Los Angeles, CA (US)

(72) Inventor: David Janow, Encinitas, CA (US)

(73) Assignee: Axiom Foods, Inc., Los Angeles, CA (US)

(*) Notice: Subject to any disclaimer, the term of this patent is extended or adjusted under 35 U.S.C. 154(b) by 345 days.

This patent is subject to a terminal disclaimer.

(21) Appl. No.: 14/199,938

(22) Filed: Mar. 6, 2014

(65) Prior Publication Data
US 2014/0255540 A1    Sep. 11, 2014

Related U.S. Application Data

(60) Provisional application No. 61/775,428, filed on Mar. 8, 2013.

(51) Int. Cl.
| | |
|---|---|
| *A23L 1/305* | (2006.01) |
| *A23L 33/00* | (2016.01) |
| *A23L 33/175* | (2016.01) |
| *A23L 33/19* | (2016.01) |

(52) U.S. Cl.
CPC .......... *A23L 33/40* (2016.08); *A23L 33/175* (2016.08); *A23L 33/19* (2016.08)

(58) Field of Classification Search
None
See application file for complete search history.

(56) References Cited

U.S. PATENT DOCUMENTS

| | | |
|---|---|---|
| 5,518,741 A | 5/1996 | Choudhury |
| 5,569,458 A | 10/1996 | Greenberg |
| 5,637,324 A | 6/1997 | Bland |
| 5,716,801 A | 2/1998 | Nielsen et al. |

(Continued)

FOREIGN PATENT DOCUMENTS

| | | |
|---|---|---|
| EP | 1112693 A1 | 7/2001 |
| EP | 1738659 A1 | 1/2007 |

(Continued)

OTHER PUBLICATIONS

Morita et al., "Mass Production Method for Rice Protein Isolate and Nutritional Evaluation"—J. Food Sci., vol. 58, No. 6, 1993, pp. 1393-1396.*

(Continued)

*Primary Examiner* — Elizabeth Gwartney
(74) *Attorney, Agent, or Firm* — Knobbe, Martens, Olson & Bear, LLP

(57) ABSTRACT

Some embodiments relate to nutritional supplements comprising rice protein isolate. Some embodiments of the nutritional supplement comprise less than about 90 mg of leucine per gram of rice protein isolate and less than about 50 mg of lysine per gram of rice protein isolate. Some embodiments pertain to methods of using the nutritional supplements described herein to achieve one or more of weight gain, weight maintenance, growth, muscle growth, muscle maintenance, decreased muscle loss, or improved exercise training results.

11 Claims, 12 Drawing Sheets

(56) References Cited

U.S. PATENT DOCUMENTS

| | | |
|---|---|---|
| 5,753,296 A | 5/1998 | Girsh |
| 5,889,040 A | 3/1999 | Beale et al. |
| 6,221,418 B1 | 4/2001 | Bergenfield et al. |
| 6,242,033 B1 | 6/2001 | Sander |
| 6,602,517 B2 | 8/2003 | Darland et al. |
| 6,713,082 B2 | 3/2004 | Siemensma et al. |
| 6,774,111 B1 | 8/2004 | Wolf et al. |
| 6,875,456 B2 | 4/2005 | Delest et al. |
| 6,923,995 B2 | 8/2005 | Highman et al. |
| 6,929,793 B2 | 8/2005 | Spivey-Krobath et al. |
| 6,989,171 B2 | 1/2006 | Portman |
| 7,097,870 B2 | 8/2006 | Funk et al. |
| 7,147,882 B2 | 12/2006 | Girsh |
| 7,220,442 B2 | 5/2007 | Gautam et al. |
| 7,563,473 B2 | 7/2009 | Scanlin et al. |
| 7,579,024 B2 | 8/2009 | Morrissey |
| 7,678,406 B2 | 3/2010 | Heydtmann et al. |
| 7,691,424 B2 | 4/2010 | Axelrod |
| 7,740,893 B2 | 6/2010 | Portman |
| 7,744,930 B2 | 6/2010 | Fisher et al. |
| 7,754,256 B2 | 7/2010 | Dennison |
| 7,759,093 B2 | 7/2010 | Callen et al. |
| 7,790,176 B2 | 9/2010 | Morrissey |
| 7,790,670 B2 | 9/2010 | Ward et al. |
| 7,790,688 B2 | 9/2010 | Wolfe et al. |
| 7,794,770 B2 | 9/2010 | Sherwood et al. |
| 7,799,363 B2 | 9/2010 | Sherwood et al. |
| 7,879,382 B2 | 2/2011 | Tuason et al. |
| 7,906,160 B2 | 3/2011 | Sherwood et al. |
| 7,943,578 B2 | 5/2011 | Ogura et al. |
| 8,017,168 B2 | 9/2011 | Prakash et al. |
| 8,178,487 B2 | 5/2012 | Boza et al. |
| 8,192,769 B2 | 6/2012 | Wester et al. |
| 8,221,817 B2 | 7/2012 | Girsh |
| 8,278,068 B2 | 10/2012 | Vielhaber et al. |
| 8,299,034 B2 | 10/2012 | Offord et al. |
| 8,383,183 B2 | 2/2013 | Prakash et al. |
| 8,425,930 B2 | 4/2013 | Barboza et al. |
| 8,445,692 B2 | 5/2013 | Karanewsky et al. |
| 8,895,088 B2 | 11/2014 | Matsunaga et al. |
| 8,956,676 B2 | 2/2015 | Hansen et al. |
| 9,034,402 B2 | 5/2015 | Wong et al. |
| 2001/0007690 A1 | 7/2001 | Girsh |
| 2001/0031729 A1 | 10/2001 | Siemensma et al. |
| 2002/0051826 A1 | 5/2002 | Darland et al. |
| 2002/0197352 A1 | 12/2002 | Portman |
| 2003/0064135 A1 | 4/2003 | Portman |
| 2003/0165606 A1 | 9/2003 | Lasekan et al. |
| 2003/0185941 A1 | 10/2003 | Highman et al. |
| 2003/0190381 A1 | 10/2003 | Bland et al. |
| 2004/0005305 A1 | 1/2004 | Spivey-Krobath et al. |
| 2004/0013771 A1 | 1/2004 | Funk et al. |
| 2004/0022926 A1 | 2/2004 | Bartocci et al. |
| 2004/0033292 A1 | 2/2004 | Portman |
| 2004/0047896 A1 | 3/2004 | Malnoe et al. |
| 2004/0067279 A1 | 4/2004 | Delest et al. |
| 2004/0131744 A1 | 7/2004 | Kunst et al. |
| 2004/0166203 A1 | 8/2004 | Gautam et al. |
| 2004/0171690 A1 | 9/2004 | Ammann et al. |
| 2004/0197380 A1 | 10/2004 | Wolf et al. |
| 2004/0219188 A1 | 11/2004 | Comer et al. |
| 2004/0220118 A1 | 11/2004 | Bland et al. |
| 2005/0002989 A1 | 1/2005 | Palmer et al. |
| 2005/0079232 A1 | 4/2005 | Offord-Cavin et al. |
| 2005/0100617 A1 | 5/2005 | Malnoe et al. |
| 2005/0106218 A1 | 5/2005 | Ward et al. |
| 2005/0152887 A1 | 7/2005 | Ernest |
| 2005/0153019 A1 | 7/2005 | Fuchs et al. |
| 2005/0181019 A1 | 8/2005 | Palmer et al. |
| 2005/0281792 A1 | 12/2005 | Short et al. |
| 2006/0019009 A1 | 1/2006 | Keller et al. |
| 2006/0034954 A1 | 2/2006 | Bland et al. |
| 2006/0088651 A1 | 4/2006 | Sandoval et al. |
| 2006/0121172 A1 | 6/2006 | Portman |
| 2006/0171993 A1 | 8/2006 | Barrett-Reis et al. |
| 2006/0182784 A1 | 8/2006 | Wester et al. |
| 2006/0193949 A1 | 8/2006 | Portman |
| 2006/0210697 A1 | 9/2006 | Mower |
| 2006/0239987 A1 | 10/2006 | Foster |
| 2006/0240169 A1 | 10/2006 | Heydtmann et al. |
| 2006/0275506 A1 | 12/2006 | Fisher et al. |
| 2006/0286279 A1 | 12/2006 | Eastman et al. |
| 2007/0092629 A1 | 4/2007 | Scanlin et al. |
| 2007/0116840 A1 | 5/2007 | Prakash et al. |
| 2007/0128333 A1 | 6/2007 | Tuason et al. |
| 2007/0141018 A1 | 6/2007 | Courtois et al. |
| 2007/0148307 A1 | 6/2007 | Sherwood et al. |
| 2007/0154614 A1 | 7/2007 | Sherwood et al. |
| 2007/0207132 A1 | 9/2007 | Speelmans et al. |
| 2008/0009440 A1 | 1/2008 | Kodera et al. |
| 2008/0020098 A1 | 1/2008 | Gautam et al. |
| 2008/0050498 A1 | 2/2008 | Sherwood et al. |
| 2008/0089961 A1 | 4/2008 | Morrissey |
| 2008/0107775 A1 | 5/2008 | Prakash et al. |
| 2008/0145511 A1 | 6/2008 | Irwin et al. |
| 2008/0206430 A1 | 8/2008 | Avila |
| 2008/0233245 A1 | 9/2008 | White et al. |
| 2008/0268038 A1 | 10/2008 | Wolfe |
| 2008/0286433 A1 | 11/2008 | Simpson et al. |
| 2008/0292765 A1 | 11/2008 | Prakash et al. |
| 2008/0299145 A1 | 12/2008 | Morrissey |
| 2009/0011083 A1 | 1/2009 | Wong et al. |
| 2009/0018196 A1 | 1/2009 | Bjork et al. |
| 2009/0053378 A1 | 2/2009 | Prakash et al. |
| 2009/0060883 A1 | 3/2009 | Offord-Cavin et al. |
| 2009/0061068 A1 | 3/2009 | Marshman et al. |
| 2009/0075862 A1 | 3/2009 | Boza et al. |
| 2009/0098261 A1 | 4/2009 | Park et al. |
| 2009/0105188 A1 | 4/2009 | Giannone et al. |
| 2009/0131331 A1 | 5/2009 | Edens et al. |
| 2009/0181903 A1 | 7/2009 | Wolfe et al. |
| 2009/0203592 A1 | 8/2009 | Beermann |
| 2009/0203606 A1 | 8/2009 | Wolfe et al. |
| 2009/0221502 A1 | 9/2009 | Yatcilla et al. |
| 2009/0238893 A1 | 9/2009 | Langford et al. |
| 2009/0269416 A1 | 10/2009 | Wedekind et al. |
| 2009/0275505 A1 | 11/2009 | Wedekind |
| 2009/0297689 A1 | 12/2009 | Edens et al. |
| 2009/0298113 A1 | 12/2009 | Vielhaber et al. |
| 2009/0298767 A1 | 12/2009 | Rowney et al. |
| 2009/0304823 A1 | 12/2009 | Offord Cavin et al. |
| 2009/0318368 A1 | 12/2009 | Ogura et al. |
| 2009/0325888 A1 | 12/2009 | Edens et al. |
| 2010/0028466 A1 | 2/2010 | Hitzfelo et al. |
| 2010/0068304 A1 | 3/2010 | Wedekind et al. |
| 2010/0068369 A1 | 3/2010 | Girsh |
| 2010/0093658 A1 | 4/2010 | Kihara et al. |
| 2010/0098802 A1 | 4/2010 | Navarro |
| 2010/0099640 A1 | 4/2010 | Geuns et al. |
| 2010/0111915 A1 | 5/2010 | Isolauri et al. |
| 2010/0112635 A1 | 5/2010 | Edens et al. |
| 2010/0113368 A1 | 5/2010 | Edens |
| 2010/0130401 A1 | 5/2010 | Wester et al. |
| 2010/0158984 A1 | 6/2010 | Qvyjt |
| 2010/0159079 A1 | 6/2010 | Qvyjt |
| 2010/0166859 A1 | 7/2010 | Edens et al. |
| 2010/0184963 A1 | 7/2010 | Scanlin et al. |
| 2010/0190708 A1 | 7/2010 | Tsuno et al. |
| 2010/0227007 A1 | 9/2010 | Romero et al. |
| 2010/0254949 A1 | 10/2010 | Barboza et al. |
| 2010/0286023 A1 | 11/2010 | Wolfe et al. |
| 2010/0297323 A1 | 11/2010 | Brooks et al. |
| 2010/0303961 A1 | 12/2010 | Brooks et al. |
| 2010/0303990 A1 | 12/2010 | Brooks et al. |
| 2010/0303991 A1 | 12/2010 | Karwowski et al. |
| 2010/0316782 A1 | 12/2010 | Shi et al. |
| 2011/0002900 A1 | 1/2011 | Mingrone et al. |
| 2011/0014328 A1 | 1/2011 | Rizvi et al. |
| 2011/0028416 A1 | 2/2011 | Offord Cavin et al. |
| 2011/0052729 A1 | 3/2011 | Golini |
| 2011/0086803 A1 | 4/2011 | De Roos et al. |
| 2011/0151097 A1 | 6/2011 | Tuason et al. |
| 2011/0152180 A1 | 6/2011 | Hettiarachchy |
| 2011/0172142 A1 | 7/2011 | Smith et al. |

(56) References Cited

U.S. PATENT DOCUMENTS

| | | |
|---|---|---|
| 2011/0189349 A1 | 8/2011 | Immig et al. |
| 2011/0233469 A1 | 9/2011 | Petersen |
| 2011/0236535 A1 | 9/2011 | Meehan |
| 2011/0250313 A1 | 10/2011 | Hwang et al. |
| 2011/0256282 A1 | 10/2011 | Piechocki et al. |
| 2011/0257087 A1 | 10/2011 | Krul et al. |
| 2011/0269185 A1 | 11/2011 | David |
| 2011/0274741 A1 | 11/2011 | Horton |
| 2011/0280988 A1 | 11/2011 | Ivy |
| 2011/0301085 A1 | 12/2011 | Wester et al. |
| 2011/0305798 A1 | 12/2011 | Steen |
| 2011/0314725 A1 | 12/2011 | Petrie et al. |
| 2011/0318464 A1 | 12/2011 | Prakash et al. |
| 2012/0027897 A1 | 2/2012 | Innocenzi |
| 2012/0039951 A1 | 2/2012 | Watson et al. |
| 2012/0040052 A1 | 2/2012 | Carrigan et al. |
| 2012/0040929 A1 | 2/2012 | Courtois et al. |
| 2012/0082760 A1 | 4/2012 | Rosedale |
| 2012/0088796 A1 | 4/2012 | Karanewsky et al. |
| 2012/0100257 A1 | 4/2012 | Lambach et al. |
| 2012/0121612 A1 | 5/2012 | Tuscano et al. |
| 2012/0122935 A1 | 5/2012 | Giannone et al. |
| 2012/0122984 A1 | 5/2012 | Hillman et al. |
| 2012/0128832 A1 | 5/2012 | Smith |
| 2012/0128851 A1 | 5/2012 | Brooks et al. |
| 2012/0141443 A1 | 6/2012 | Prioult et al. |
| 2012/0149782 A1 | 6/2012 | Hitzfeld et al. |
| 2012/0164306 A1 | 6/2012 | Girsh |
| 2012/0171165 A1 | 7/2012 | Buck et al. |
| 2012/0171166 A1 | 7/2012 | Chow et al. |
| 2012/0171177 A1 | 7/2012 | Biehl et al. |
| 2012/0171178 A1 | 7/2012 | Fleith et al. |
| 2012/0172319 A1 | 7/2012 | Chow et al. |
| 2012/0177752 A1 | 7/2012 | Baxter et al. |
| 2012/0178672 A1 | 7/2012 | Wolf et al. |
| 2012/0183506 A1 | 7/2012 | Nutten et al. |
| 2012/0189715 A1 | 7/2012 | Baxter et al. |
| 2012/0189716 A1 | 7/2012 | Baxter et al. |
| 2012/0189717 A1 | 7/2012 | Baxter et al. |
| 2012/0196352 A1 | 8/2012 | Kim et al. |
| 2012/0196829 A1 | 8/2012 | Baxter et al. |
| 2012/0207882 A1 | 8/2012 | Sonnenburg |
| 2012/0207904 A1 | 8/2012 | Twombly et al. |
| 2012/0244125 A1 | 9/2012 | Verdu de Bercik et al. |
| 2012/0251512 A1 | 10/2012 | Farmer et al. |
| 2012/0276057 A1 | 11/2012 | Steenhout et al. |
| 2012/0282232 A1 | 11/2012 | Tobin et al. |
| 2012/0283180 A1 | 11/2012 | Hofman et al. |
| 2012/0288588 A1 | 11/2012 | Barron |
| 2012/0309092 A1 | 12/2012 | Spangenberg et al. |
| 2012/0315697 A1 | 12/2012 | Pettit et al. |
| 2012/0322992 A1 | 12/2012 | Ochiai et al. |
| 2012/0329756 A1 | 12/2012 | Courtois et al. |
| 2013/0011498 A1 | 1/2013 | Baxter et al. |
| 2013/0023468 A1 | 1/2013 | Hofman et al. |
| 2013/0052234 A1 | 2/2013 | Goldberg et al. |
| 2013/0065822 A1 | 3/2013 | Miller et al. |
| 2013/0090391 A1 | 4/2013 | Tan et al. |
| 2013/0101697 A1 | 4/2013 | Shimada et al. |
| 2013/0115329 A1 | 5/2013 | Savant et al. |
| 2013/0115330 A1 | 5/2013 | Savant et al. |
| 2013/0122139 A1 | 5/2013 | Savant et al. |
| 2013/0122148 A1 | 5/2013 | Savant et al. |
| 2013/0122180 A1 | 5/2013 | Brooks et al. |
| 2013/0129838 A1 | 5/2013 | Miller et al. |
| 2013/0129868 A1 | 5/2013 | Gulseren et al. |
| 2013/0130972 A1 | 5/2013 | Le Coutre et al. |
| 2013/0142903 A1 | 6/2013 | Duan et al. |
| 2013/0160165 A1 | 6/2013 | Reuzeau et al. |
| 2013/0171318 A1 | 7/2013 | Bovetto et al. |
| 2013/0195803 A1 | 8/2013 | German et al. |
| 2013/0202764 A1 | 8/2013 | Prakash et al. |
| 2013/0203645 A1 | 8/2013 | Moore et al. |
| 2013/0203663 A1 | 8/2013 | Mager et al. |
| 2013/0209373 A1 | 8/2013 | Mager et al. |
| 2013/0209587 A1 | 8/2013 | Mager et al. |
| 2014/0205710 A1 | 7/2014 | Janow |

FOREIGN PATENT DOCUMENTS

| | | |
|---|---|---|
| JP | 2007-222053 A | 9/2007 |
| WO | WO 95/03708 A1 | 2/1995 |
| WO | WO 96/19120 A1 | 6/1996 |
| WO | WO 96/34535 A1 | 11/1996 |
| WO | WO 2000/057711 A1 | 10/2000 |
| WO | WO 2004/047549 A1 | 6/2004 |
| WO | WO 2006/047352 A1 | 5/2006 |
| WO | WO 2007/035595 A1 | 3/2007 |
| WO | WO 2008/144259 A1 | 11/2008 |
| WO | WO 2010/071541 | 6/2010 |
| WO | WO 2011/089525 A2 | 7/2011 |
| WO | WO 2011/149713 | 12/2011 |
| WO | WO 2012/024611 A1 | 2/2012 |
| WO | WO 2012/051591 A2 | 4/2012 |
| WO | WO 2012/106179 A1 | 8/2012 |
| WO | WO 2012/130627 A1 | 10/2012 |
| WO | WO 2012/135499 A1 | 10/2012 |
| WO | WO 2012/141795 A1 | 10/2012 |
| WO | WO 2012/170021 A1 | 12/2012 |
| WO | WO 2013/092851 A1 | 6/2013 |
| WO | WO 2014/138304 | 9/2014 |

OTHER PUBLICATIONS

Axiom Foods, "Oryzatein® 80: Original, Silk, Ultra-Amino Acid Profile", Sep. 29, 2015, p. 1.*

Barber, S., Studies on the chemistry and technology of foods, Valencia [Spain], Revista de Agroquimica y Tecnologia de Alimentos (1981), 21(2), 175-84.

Chen et al., Preparation and development of rice bran beverage, Shipin Keji (2012), 37(9), 156-159, 165.

Dapra et al., Rice protein-concentrate meal as a potential dietary ingredient in practical diets for blackspot seabream Pagellus bogaraveo: a histological and enzymatic investigation, Journal of Fish Biology, (2009) vol. 74, No. 4, pp. 773-789.

Fujital et al., Effect of quality and quantity of dietary protein on free amino acids in plasma and tissues of adult rats, Nutr. Res. Lab., Tokyo Metrop. Inst. Gerontol., Tokyo, 173, Japan.

Hou et al., Rice protein concentrate partially replaces dried whey in the diet for early-weaned piglets and improves their growth performance, (2008), J. Sci. Food Agric., 88: 1187-1193.

Huang et al., Effects of rice-duck ecological management technique on growth performance and meat quality of ducks, Hunan Nongye Daxue Xuebao (2007), 33(6), 714-717.

Ishii et al., A rice diet is associated with less fat synthesis/accumulation than a bread diet before exercise therapy, Journal of Nutritional Science and Vitaminology (2005), 51(5), 349-354.

Joy et al., The effects of 8 weeks of whey or rice protein supplementation on body composition and exercise performance, 2013, Nutritional Journal, pp. 1-7, 12:86.

Kadekaru et al., Rice protein and peptide for sports nutrition, Food Style 21 (2012), 16(4), 66-68.

Katz et al., Rice nightmare: Kwashiorkor in 2 Philadelphia-area infants fed Rice Dream beverage, Journal of the American Academy of Dermatology, (May 2005) vol. 52, No. 5 Suppl. 1, pp. S69-S72.

Kikuchi, Mitsori, The functionality of rice protein and rice peptide, Food Style 21 (2009), 13(11), 69-71.

Knott, M., Mainstream Muscle, Food Manufacture, 2012, (Nov.), 87 (11), 55-56.

Li et al., Effects of rice dreg protein and its hydrolysate on growth performance and small intestine morphology of early-weaned rats, J. Sci. Food Agric., 2011, 91: 687-693.

Liu et al., Advances on biosynthesis of rice seed storage proteins in molecular biology, Fenzi Zhiwu Yuzhong (2008), 6(1), 1-15.

Milo Ohr, L., Nutraceuticals and functional foods, Food Technology, 2005, (Jun.), 59 (6), 84-100, Published by: Institute of Food Technologists.

(56) References Cited

OTHER PUBLICATIONS

Mizukami et al., Effect of vegetable protein fed to pregnant rats on the growth of the young and their improved nutrition, Nippon Kasei Gakkaishi (1992), 43(7), 617-27.
Noel et al., A traditional rice and beans pattern is associated with metabolic syndrome in Puerto Rican older adults, Journal of Nutrition (2009), 139(7), 1360-1367.
Omstedt et al., Effect of the nutritional value of dietary proteins on the synthesis of proteins in skeletal muscle, Naeringsforskning (1972), 16(4), 193-202.
Omstedt et al., The influence of the nutritive value of proteins on the level of protein synthesis in vitro in rat skeletal muscle, Br. J. Nutr. (1972), 27, 467-474.
Oujifard et al., Fish meal replacement with rice protein concentrate in a practical diet for the Pacific white shrimp, *Litopenaeus vannamei* Boone, 1931, Aquaculture International, Feb. 2012, vol. 20, Issue 1, pp. 117-129.
Palmegiano et al., Rice protein concentrate meal as potential dietary ingredient in practical diets for blackspot seabream (Pagellus bogaraveo), Journal of Animal Physiology and Animal Nutrition(2007), 91(5-6), 235-239.
Palmegiano et al., Rice protein concentrate meal as potential dietary ingredient in practical diets for rainbow trout, (Oncorhynchus mykiss), Aquaculture (2006), 258(1-4), 357-367.
Santana et al., Naturally occurring ingredients as potential antiaging cosmetics, Latin American Journal of Pharmacy (2011), 30(8), 1531-1535.
Suh, Succ Jo, Effects of rice diet on rats, K'at'ollik Taehak Uihakpu Nonmunjip (1963), 7, 1-31.
Tanphaichitr et al., Dietary lysine and carnitine: relation to growth and fatty livers in rats, Journal of Nutrition (1976), vol. 106, No. 1, pp. 111-117.
Tome, Daniel, Criteria and markers for protein quality assessment—a review, British Journal of Nutrition, 2012, 108, S222-S229.
Vijayaraghavan, P. K., Hemopoietic activity of food proteins, Indian Journal of Medical Research (1913-1988), (1955),43, 569-74.
Wang et al., Beverage based on rice and soybean water-soluble extract, Ciencia e Tecnologia de Alimentos (1997), 17(2), 73-77.
Yengkokpam et al., Gelatinized carbohydrates in the diet of Catla catla fingerlings: effect of levels and sources on nutrient utilization, body composition and tissue enzyme activities, Asian-Australasian Journal of Animal Sciences (2007),20(1), 89-99.
Yin, Li-Jung, Effect of rice koji fermentation on the characteristics of mackerel muscle, Taiwan Shuichan Xuehuikan (2005), 32(4), 341-354.
Zazula, Magdalena, Changes in body protein level in tree sparrow (*Passer montanus* (L.)) induced by high and low protein diets, Ekologia Polska (1984), 32(4), 709-20.
International Preliminary Report on Patentability received in PCT Application No. PCT/US2014/20915, dated Sep. 17, 2015 in 8 pages.
Jäger et al., "Comparison of Rice and Whey Protein Osolate Digestion Rate and Amino Acid Absorption", Journal of the International Society of Sports Nutrition, 2013, vol. 10, Suppl. 1, pp. 3.
Kikuchi, Mitsori, "The Functionality of Rice Protein and Rice Peptide," Food Style 21, 2009, vol. 13 No. 11, pp. 69-71.
Koo et al. "Rice Protein-Based Infant Formula: Current Status and Future Development", Minerva Pediatrics, 2007, vol. 59, No. 1, pp. 35-41.
Weiner et al., "Rice Protein Increases Lean Body Mass, Muscle Hypertrophy, Power and Strength Comparable to Whey Protein Following Resistance Exercise," Poster presented at NSCA National Conference, Las Vegas, Jul. 10-13, 2013, pp. 3.
Rich Gaspari, Clinical Muscle Presents Brown Rice Protein Concentrate by Rich Gaspari, single screen shot, YouTube Video indicates an upload of Jan. 20, 2012.
Roohinejad, et al. (2011). Effect of Pre-Germination Time on Amino Acid Profile and Gamma Amino Acid (GABA) Contents in Different Varieties of Malaysian Brown Rice. Int'l J. Food Properties, 14:6, 1386-1399.
Amazon.com, "Growing Naturals Rice Protein Isolate Powder, Vanilla Blast, 16.4 Ounce", Growing Naturals, http://www.amazon.com/Growing-Naturals-Protein-lsolate-Vanilla/dp/B005K0MFSA [See description of product], as printed Jun. 9, 2016 in 6 pages.
Campbell et al., "International Society of Sports Nutrition Position Stand: Protein and Exercise", Journal of the International Society of Sports Nutrition, Sep. 26, 2007, vol. 4, No. 8, pp. 7.
International Search Report and Written Opinion of the International Searching Authority dated May 30, 2014 for International Application No. PCT/US2014/20915.
Santos, et al. (Jan. 2013). Storage Protein profile and amino acid content in wild rice *Oryza glumaepatula*. Pes. Agrpec. Bras., Brasilia, v. 48, n. 1, 66-72.†
Houston et al. (1969). Amino Acid Composition of Rice and Rice By-Products. Cereal Chem. 46:527-537.†

\* cited by examiner
† cited by third party

FIG. 1A

RICE PROTEIN SUPPLEMENT AND METHODS OF USE THEREOF

CROSS-REFERENCE TO RELATED APPLICATIONS

This patent application claims the benefit of priority to U.S. Provisional Patent Application No. 61/775,428, filed Mar. 8, 2013. The foregoing application is fully incorporated herein by reference for all purposes.

BACKGROUND OF THE INVENTION

Field of the Invention

Disclosed herein are nutritional supplements comprising rice protein isolate and methods of use thereof. In some embodiments, the use of rice protein leads to one or more of weight gain, weight maintenance, growth, muscle growth, muscle maintenance, decreased muscle loss, and/or improved exercise training results.

Description of the Related Art

Recommended levels for an adequate dietary protein intake for an adult is 0.8 grams per kilogram of body weight, the average daily intake level that is sufficient to meet the nutrient requirement of nearly all healthy individuals. The protein requirements are based on nitrogen balance, trying to achieve a balance between nitrogen intake and excretion. Protein recommendations for endurance and strength trained athletes range from 1.2 to 2.0 g/kg/d, reflecting the athlete's nutritional goal to increase lean body mass. The athlete has a choice of different animal (e.g. whey, casein) or plant protein (e.g. soy) sources, differing in numerous ways such as the presence of allergens (lactose, soy), cholesterol, saturated fats, digestion rate (fast, intermittent, slow absorption of amino acids), or the relative amount of individual amino acids.

SUMMARY

Certain aspects of the disclosure are directed to a nutritional supplement comprising a rice protein isolate. In some embodiments, the nutritional supplement comprises less than about 90 mg of leucine per gram of rice protein isolate. In some embodiments, the nutritional supplement comprises less than about 50 mg of lysine per gram of rice protein isolate of rice protein isolate.

Certain aspects of the disclosure are directed to a nutritional supplement comprising a rice protein isolate. In some embodiments, the nutritional supplement comprises less than about 95 mg of leucine per gram of rice protein isolate. In some embodiments, the nutritional supplement comprises less than about 55 mg of lysine per gram of rice protein isolate of rice protein isolate.

Any embodiment described above, or described elsewhere herein, can include one or more of the following features.

In some embodiments, the nutritional supplement comprises less than about 50 mg of isoleucine per gram of rice protein isolate.

In some embodiments, the nutritional supplement comprises less than about 60 mg of valine per gram of rice protein isolate.

In some embodiments, each gram of the rice protein isolate comprises between about 45 mg and about 60 mg alanine, between about 65 mg and 85 mg arginine, between about 75 mg and about 95 mg aspartic acid, between about 15 mg and about 25 mg cysteine, between about 165 mg and 185 mg of glutamic acid, about 30 mg and about 55 mg glycine, between about 15 mg and about 25 mg histidine, between about 35 mg about 60 mg isoleucine, between about 75 mg and about 95 mg of leucine, between about 25 mg and about 55 mg lysine, between about 20 mg and about 35 mg of methionine, between about 50 mg and about 60 mg phenylalanine, between about 40 and about 65 mg proline, between about 45 mg and about 55 mg serine, between about 35 mg and about 50 mg threonine, between about 10 mg and about 20 mg tryptophan, between about 40 mg and about 55 mg tyrosine, and between about 55 mg and about 65 mg of valine.

In some embodiments, each gram of the rice protein isolate comprises about 54 mg alanine, about 77 mg arginine, about 87 mg aspartic acid, about 21 mg cysteine, about 174 mg glutamic acid, about 43 mg glycine, about 22 mg histidine, about 41 mg isoleucine, about 80 mg leucine, about 31 mg lysine, about 28 mg methionine, about 53 mg phenylalanine, about 45 mg proline, about 49 mg serine, about 35 mg threonine, about 14 mg tryptophan, about 47 mg tyrosine, and about 58 mg valine per gram of protein.

In some embodiments, the nutritional supplement further comprises organic sprouted whole grain brown rice syrup solids.

In some embodiments, the nutritional supplement further comprises one or more of organic flavor, organic guar gum, organic gum arabic, organic stevia, sea salt, and organic sunflower oil.

In some embodiments, the rice protein isolate is a brown rice protein isolate.

In some embodiments, the nutritional supplement has about 70.5 mg leucine and about 39.6 mg lysine per gram dry weight of the nutritional supplement.

In some embodiments, the nutritional supplement comprises less than about 95 mg of leucine per gram of protein in the rice protein isolate. In some embodiments, the nutritional supplement comprises less than about 55 mg of lysine per gram of protein in rice protein isolate of rice protein isolate.

Certain aspects of the disclosure are directed to methods of improving a result of exercise training. In some embodiments, the method comprising providing the nutritional supplement described above or below to a subject, wherein ingestion of an effective amount of the nutritional supplement by the subject before, during or after exercise training results in at least one of increased muscle mass, increased strength, increased power, improved body composition, increased VO2 max, increased endurance, decreased fat mass, and decreased body weight.

Certain aspects of the disclosure are directed to methods of supplementing the diet of a subject. In some embodiments, the method comprises providing the nutritional supplement described above or below to a subject, wherein the subject is a newborn, infant, toddler, child, adolescent, adult, or a geriatric individual, wherein ingestion of an effective amount of the nutritional supplement by the subject results in at least one of weight gain, weight maintenance, growth, muscle growth, muscle maintenance, decreased muscle loss, improved recovery after exercise training, decreased recovery time associated with exercise training, decreased muscle soreness associated with exercise training, decreased fat mass, and maintaining nitrogen balance.

Certain aspects of the disclosure are directed to methods of increasing the satiety in a subject. In some embodiments, using a nutritional supplement comprising a rice protein isolate as described above or below increases satiety in comparison to a nutritional supplement containing whey protein isolate. In some embodiments, the period time of satiation using a rice protein isolate is increased by about 5, 10, 15, 20, 25, 30, 35, 40, 50, or more than 50% relative to whey protein isolate having an equivalent amount of protein. In some embodiments, the method comprises providing the nutritional supplement comprising rice protein isolate described above or below to a subject.

In some embodiments, the Tmax of leucine is between about 50 minutes and about 70 minutes.

Certain aspects of the disclosure are directed to methods of increasing the satiety in a subject. In some embodiments, ingesting a nutritional supplement comprising a rice protein isolate, as described above or below, increases the satiety of a subject in comparison to ingesting a nutritional supplement containing whey protein isolate. In some embodiments, the period time of satiation using a rice protein isolate is increased by about 5, 10, 15, 20, 25, 30, 35, 40, 50, or more than 50% relative to whey protein isolate having an equivalent amount of protein. In some embodiments, the method comprises providing the nutritional supplement comprising rice protein isolate described above or below to a subject.

Certain aspects of the disclosure are directed to methods for improving a result of exercise training in a subject. In some embodiments, the method comprises providing a nutritional supplement comprising a rice protein isolate, wherein ingestion of an effective amount of the nutritional supplement by the subject before, during or after exercise training results in at least one of increased muscle mass, increased strength, increased power, improved body composition, increased VO2 max, and increased endurance.

Any of the method described above, or described elsewhere herein, can include one or more of the following features.

In some embodiments of the method, the rice protein isolate comprises less than about 90 mg of leucine per gram of dry nutritional supplement and less than about 50 mg of lysine per gram of dry nutritional supplement.

In some embodiments of the method, the rice protein isolate comprises less than about 50 mg of isoleucine and less than about 60 mg of valine per gram of dry nutritional supplement.

In some embodiments of the method, the improved result of resistance training comprises increased skeletal muscle hypertrophy.

In some embodiments of the method, the improved result of resistance training comprises an increase in strength.

In some embodiments of the method, the improved result of resistance training comprises an increase in power.

In some embodiments of the method, the improved result of resistance training comprises improved body composition. In some embodiments, an improved body composition can be a decrease in the ratio of fat to muscle in a patient.

In some embodiments of the method, the improved result of resistance training comprises an increase VO2 max.

In some embodiments of the method, the improved result of resistance training comprises an increase in exercise duration and/or exercise performance.

Certain aspects of the disclosure are directed to methods of supplementing the diet of a subject. In some embodiments, the method comprises providing a nutritional supplement comprising a rice protein isolate to a subject, wherein the subject is a newborn, infant, toddler, child, adolescent, adult, or geriatric individual, wherein ingestion of an effective amount of the nutritional supplement by the subject results in at least one of weight gain, weight maintenance, growth, muscle mass growth, muscle maintenance, muscle mass maintenance, and/or decreased loss of muscle mass.

In some embodiments of the method, the rice protein isolate comprises less than about 90 mg of leucine per gram of dry nutritional supplement and less than about 50 mg of lysine per gram of dry nutritional supplement.

In some embodiments, the method of supplementing a subject's diet comprises providing a nutritional supplement comprising a rice protein isolate to a subject, wherein the subject is a newborn, infant, toddler, child, adolescent, adult, or geriatric individual, wherein ingestion of an effective amount of the nutritional supplement by the subject results in results in maintaining nitrogen balance in the subject.

BRIEF DESCRIPTION OF THE DRAWINGS

Figure 1A:
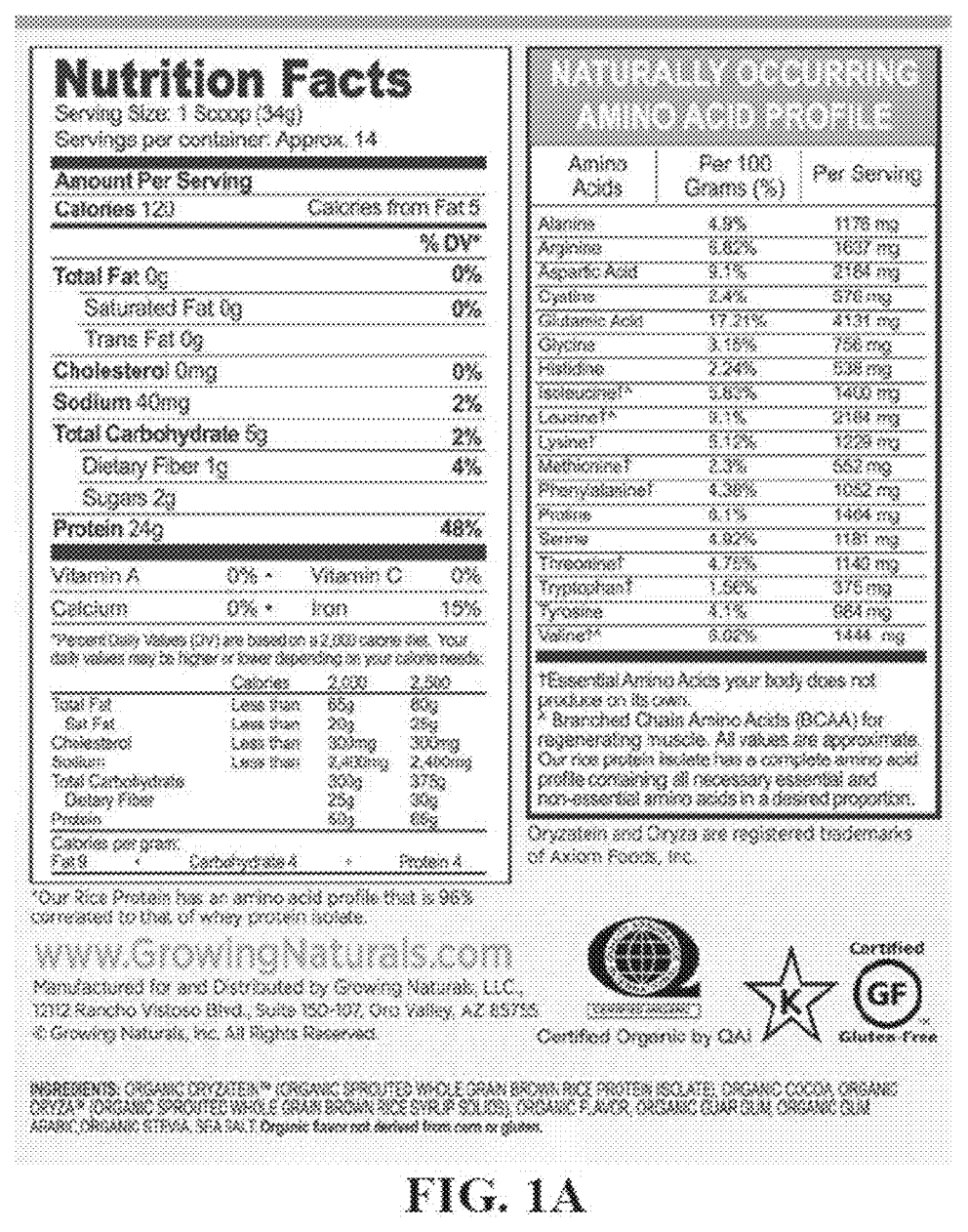

FIGS. 1A-1B depict product labels for Growing Naturals Rice Protein Isolate and for Nutra Bio Whey Protein Isolate, respectively.

DETAILED DESCRIPTION

Figure 1B:

Complete proteins, such as animal- or dairy-derived (e.g. meat, egg, and whey proteins), are proteins having adequate proportions of each of the nine essential amino acid (histidine, isoleucine, leucine, lysine, methionine, phenylalanine, threonine, tryptophan, and valine). As complete proteins, these sources meet the dietary needs of animals. Complete proteins allow muscle growth, muscle maintenance, nutritional balance, weight gain, and weight maintenance. Because they provide a complete amino acid profile, complete proteins are the proteins of choice for doctors seeking to supplement the diets of infants and geriatric patients in danger of losing weight or unable to sustain weight gain. Complete proteins are also the first choice for athletes (and their trainers) seeking to improve the results of exercise training.

Rice proteins, alternatively, are "incomplete proteins." As "incomplete proteins," rice proteins are deficient in one or more essential amino acids. Rice protein specifically lacks sufficient amounts of threonine and lysine and, in comparison to whey protein, contains lower amounts of leucine. Rice protein also has lower protein quality (i.e. proportion of digestible protein) relative to many complete proteins. For example, rice protein is only about 87% digestible relative to casein. Rice protein is also slower absorbing than other proteins, discouraging its use. Thus, the use of rice protein in dietary supplementation has been discouraged.

For instance, rice protein, by itself, is thought to be an inadequate protein source for protein-based infant formulas. In order to reach acceptable essential amino acid levels, rice protein in infant formula is often fortified with other amino acids to enhance their nutritive value. Some researchers have even sought to genetically engineer rice to improve the proportional ratio of essential amino acids in rice protein isolates.

For the same reasoning, rice protein sources have been avoided in the formulation of exercise supplements. Long term, periodized resistance training (RT) results in increases in skeletal muscle size and, ultimately, force generating capacity. Sports nutrition scientists have attempted to increase training induced gains through a number of protocols, which generally attempt to augment and/or speed skeletal muscle regeneration. One such intervention has been to increase the provision of the branched chain amino acids (BCAAs), leucine, isoleucine, and valine, which make up more than one third of muscle protein(s). By providing complete protein sources before, during, and/or after exercise, sufficient levels of leucine, isoleucine, and valine are present to allow muscle growth. The BCAAs are unique among the essential amino acids (EAAs) for their roles in protein metabolism, neural function, and blood glucose and insulin regulation. In some studies, researchers have shown that BCAAs potentially are able to stimulate skeletal muscle protein synthesis (MPS) to the same degree as all the combination of all nine essential amino acids. Leucine may play the most important role in muscle growth, as it is the only BCAA that was able to independently stimulate MPS.

It is well known that vigorous exercise can induce a net negative protein balance in response to both endurance and resistance training. Researchers have proposed that consumption of BCAAs, namely leucine, could turn individuals from a negative to a positive whole-body protein balance after intense exercise. In support, the consumption of a protein or EAA complex that contains sufficient leucine has been shown to shift protein balance to a net positive state after intense exercise training. These findings led researchers to suggest that optimal protein intake per meal should be based on the leucine content of the protein consumed.

Rice-based proteins, with as low as 55% of the leucine content of animal-based proteins, have not been shown to increase MPS compared to animal-based proteins (i.e. plant-based proteins have as little as 6% leucine and animal-based proteins contain as much as 11% leucine). Moreover at lower doses of protein (10% of energy), animal sources stimulate MPS to a greater degree than plant sources. Similar to the results achieved with the fortification of baby formulas, by fortifying plant-based proteins with the deficient amino acids, MPS comparable to that from animal protein supplementation can be achieved with plant-based proteins.

An unmet need in the area of protein supplementation exists for a non-allergenic protein source that provides an amino acid profile sufficient to improve the results of athletic training and to allow weight maintenance and/or gain in infant and geriatric patients. Surprisingly, it has now been found that the particular rice protein isolate described herein is a suitable form of protein to support muscle hypertrophy in combination with athletic training. It has been found that rice protein isolate is actually comparable to whey protein in its effects on lean mass and strength when given following RT. These results are especially important given that food allergies may force some subjects to abandon the use of milk (human or cow) and soy products. The rice protein lysate described herein, an allergen-free protein source, may offer an alternative to these other protein sources. The rice protein lysates described herein may also be appropriate for helping increase weight gain, preventing weight loss, and meeting the nutritive demands in infants and geriatric patients. Furthermore, as a vegan protein source, the rice protein isolates described herein may offer vegetarian and vegan people a way to increase their protein intake.

A variety of embodiments and methods are described below to illustrate various examples that may be employed to achieve one or more desired improvements. These examples are only illustrative and not intended in any way to restrict the general inventions presented and the various aspects and features of these inventions. Furthermore, the phraseology and terminology used herein is for the purpose of description and should not be regarded as limiting. No features, structure, or step disclosed herein is essential or indispensible.

As used herein, the term "exercise training" includes resistance training, endurance training, speed training, metabolic conditioning, participation in sports, obstacle courses, endurance races, middle distance races, sprint races, weightlifting, Olympic weightlifting, body building, running, gymnastics, combinations thereof, and any other activity that requires muscular and cardiovascular effort.

As used herein, the term "harvested" means that at least a portion of the original carbohydrate, fat, and/or mineral content has been removed, for example, from a naturally occurring protein source. A protein that has been harvested has an increased concentration (by weight) relative to an unharvested protein.

As used herein, the term "protein isolate" is to be interpreted broadly and includes compositions containing protein (including intact proteins, polypeptides, oligopeptides, and/or amino acids) that have been harvested from naturally occurring protein sources (e.g. rice, soy, whey, milk, meat, etc.). The term protein isolate includes concentrates and hydrolysates of protein from naturally occurring protein sources. The term protein isolate also may include amino acids (whether in monomeric, oligomeric, or polymeric form) that have been concentrated or processed from their native sources via hydrolysis, enzymatic degradation, fermentation, and/or other techniques. In some embodiments, a protein isolate comprises at least about 30%, 40%, 50%, 60%, 70%, 80%, or 90% protein by weight. In some embodiments, a protein isolate comprises at least about 90% protein by weight.

As used herein, the term "protein concentrate" means compositions containing protein (including intact proteins, polypeptides, oligopeptides, and/or amino acids) that have been harvested from naturally occurring protein sources and that have at least 80% protein by weight.

As used herein, the term "protein" is to be interpreted broadly and includes intact proteins, polypeptides, oligopeptides, amino acids, and mixtures thereof.

As used herein, the term "animals" is to be interpreted broadly and includes, but is not limited to mammals, such as, humans, mice, rats, cats, dogs, livestock (e.g. pigs, cows), horses, monkeys, and apes, birds (e.g. chickens), reptiles, and amphibians.

As used herein, the term "subject" is to be interpreted broadly and includes animals, patients, athletes, and infants who are capable of ingesting rice protein hydrosylate.

As used herein, the term "athlete" is given its ordinary definition and also broadly includes people performing exercise for training, maintaining health, general health improvement, and for rehabilitation.

As used herein, the term "geriatric" is given its plain and ordinary meaning and is intended to include people over the age of 60.

As used herein, the term "dry weight" means the weight of a solid, semi-solid, or oil without added water.

Nutritional Compositions

In some embodiments, a nutritional supplement comprising a rice-derived protein isolate (or rice protein isolate) is provided. In some embodiments, the rice-derived protein isolate is derived from a brown rice. In some embodiments, the brown rice is a whole grain brown rice. In some embodiments, the source of protein within the nutritional supplement consists only of rice protein isolate.

In some embodiments, the nutritional supplement comprises less than about 90 mg of leucine per gram of rice protein isolate. In some embodiments, the nutritional supplement comprises less than about 115, 110, 100, 95, 90, 85, 80, 70, 60, 50, 40, 30, 20, or 10 mg of leucine per gram rice protein isolate. In some embodiments, the nutritional supplement comprises less than about 95 mg of leucine per gram of protein in the rice protein isolate. In some embodiments, the nutritional supplement comprises less than about 115, 110, 100, 95, 90, 85, 80, 70, 60, 50, 40, 30, 20, or 10 mg of leucine per gram of protein in the rice protein isolate. In some embodiments, each gram of the rice protein isolate comprises between about 0 mg and about 5 mg, about 5 mg and about 15 mg, about 15 mg and about 25 mg, about 25 mg and about 35 mg, about 35 mg and about 45 mg, about 45 mg and about 55 mg, about 55 mg and about 65 mg, about 65 mg and about 75 mg, about 75 mg and about 85 mg, about 85 mg and about 95 mg, about 95 mg and about 105 mg, or about 105 mg and about 115 mg of leucine. In some embodiments, each gram of the nutritional supplement comprises about 80 mg of leucine.

In some embodiments, the nutritional supplement comprises less than about 50 mg of lysine per gram of rice protein isolate. In some embodiments, the nutritional supplement comprises less than about 110, 100, 90, 80, 70, 60, 55, 50, 45, 40, 35, 30, 20, or 10 mg of lysine per gram of rice protein isolate. In some embodiments, the nutritional supplement comprises less than about 55 mg of lysine per gram of protein in the rice protein isolate. In some embodiments, the nutritional supplement comprises less than about 110, 100, 90, 80, 70, 60, 55, 50, 45, 40, 35, 30, 20, or 10 mg of lysine per gram of protein in the rice protein isolate. In some embodiments, each gram of the rice protein isolate comprises between about 0 mg and about 5 mg, about 5 mg and about 15 mg, about 15 mg and about 25 mg, about 25 mg and about 35 mg, about 35 mg and about 45 mg, about 45 mg and about 55 mg, about 55 mg and about 65 mg, about 65 mg and about 75 mg, about 75 mg and about 85 mg, about 85 mg and about 95 mg, or about 95 mg and about 105 mg of lysine. In some embodiments, each gram of the nutritional supplement comprises about 31 mg of lysine.

In some embodiments, the nutritional supplement comprises less than about 50 mg of isoleucine per gram of rice protein isolate. In some embodiments, the nutritional supplement comprises less than about 70, 60, 50, 40, 30, 20, or 10 mg of isoleucine per gram of rice protein isolate. In some embodiments, each gram of the rice protein isolate comprises between about 0 mg and about 5 mg, about 5 mg and about 15 mg, about 15 mg and about 25 mg, about 25 mg and about 35 mg, about 35 mg and about 45 mg, about 45 mg and about 55 mg, about 55 mg and about 65 mg, or about 65 mg and about 75 mg of isoleucine. In some embodiments, each gram of the nutritional supplement comprises about 41 mg of isoleucine.

In some embodiments, the nutritional supplement comprises less than about 60 mg of valine per gram of rice protein isolate. In some embodiments, the nutritional supplement comprises less than about 70, 60, 50, 40, 30, 20, or 10 mg of valine per gram of rice protein isolate. In some embodiments, each gram of the rice protein isolate comprises between about 0 mg and about 5 mg, about 5 mg and about 15 mg, about 15 mg and about 25 mg, about 25 mg and about 35 mg, about 35 mg and about 45 mg, about 45 mg and about 55 mg, about 55 mg and about 65 mg, or about 65 mg and about 75 mg of valine. In some embodiments, each gram of the nutritional supplement comprises about 58 mg of valine.

In some embodiments, the nutritional supplement comprises less than about 80 mg of threonine per gram of rice protein isolate. In some embodiments, the nutritional supplement comprises less than about 80, 70, 60, 50, 40, 30, 20, or 10 mg of threonine per gram of rice protein isolate. In some embodiments, each gram of the rice protein isolate comprises between about 0 mg and about 10 mg, about 10 mg and about 20 mg, about 20 mg and about 30 mg, about 30 mg and about 40 mg, about 40 mg and about 50 mg, about 50 mg and about 60 mg, about 60 mg and about 70 mg, or about 70 mg and about 80 mg of threonine. In some embodiments, each gram of the nutritional supplement comprises about 35 mg of threonine.

In some embodiments, the nutritional supplement comprises less than about 60 mg of alanine per gram of rice protein isolate. In some embodiments, the nutritional supplement comprises less than about 60, 50, 40, 30, 20, or 10 mg of alanine per gram of rice protein isolate. In some embodiments, each gram of the rice protein isolate comprises between about 0 mg and about 10 mg, about 10 mg and about 20 mg, about 20 mg and about 30 mg, about 30 mg and about 40 mg, about 40 mg and about 50 mg, or about 50 mg and about 60 mg of alanine. In some embodiments, each gram of the nutritional supplement comprises about 54 mg of alanine.

In some embodiments, the nutritional supplement comprises greater than about 80 mg of arginine per gram of rice protein isolate. In some embodiments, the nutritional supplement comprises greater than about 80, 70, 60, 50, 40, 30, 20, or 10 mg of arginine per gram of rice protein isolate. In some embodiments, each gram of the rice protein isolate comprises between about 0 mg and about 10 mg, about 10 mg and about 20 mg, about 20 mg and about 30 mg, about 30 mg and about 40 mg, about 40 mg and about 50 mg, about 50 mg and about 60 mg, about 60 mg and about 70 mg, about 70 mg and about 80 mg, or about 80 mg and about 90 mg of arginine. In some embodiments, each gram of the nutritional supplement comprises about 77 mg of arginine.

In some embodiments, the nutritional supplement comprises less than about 120 mg of aspartic acid per gram of rice protein isolate. In some embodiments, the nutritional supplement comprises less than about 120, 110, 100, 90, 80, 70, 60, 50, 40, 30, 20, or 10 mg of aspartic acid per gram of rice protein isolate. In some embodiments, each gram of the rice protein isolate comprises between about 0 mg and about 10 mg, about 10 mg and about 20 mg, about 20 mg and about 30 mg, about 30 mg and about 40 mg, about 40 mg and about 50 mg, about 50 mg and about 60 mg, about 60 mg and about 70 mg, about 70 mg and about 80 mg, about 80 mg and about 90 mg, about 90 mg and about 100 mg, about 100 mg and about 110 mg, or about 110 mg and about 120 mg of aspartic acid. In some embodiments, each gram of the nutritional supplement comprises about 87 mg of aspartic acid.

In some embodiments, the nutritional supplement comprises less than about 30 mg of cysteine per gram of rice protein isolate. In some embodiments, the nutritional supplement comprises less than about 40, 30, 20, or 10 mg of cysteine per gram of rice protein isolate. In some embodiments, each gram of the rice protein isolate comprises between about 0 mg and about 5 mg, about 5 mg and about 15 mg, about 15 mg and about 25 mg, or about 25 mg and about 35 mg of cysteine. In some embodiments, each gram of the nutritional supplement comprises about 21 mg of cysteine.

In some embodiments, the nutritional supplement comprises less than about 180 mg of glutamic acid per gram of rice protein isolate. In some embodiments, the nutritional supplement comprises less than about 200, 190, 180, 170, 160, 150, 140, 130, 120, 110, 100, 90, 80, 70, 60, 50, 40, 30, 20, or 10 mg of glutamic acid per gram of rice protein isolate. In some embodiments, each gram of the rice protein isolate comprises between about 0 mg and about 10 mg, about 10 mg and about 20 mg, about 20 mg and about 30 mg, about 30 mg and about 40 mg, about 40 mg and about 50 mg, about 50 mg and about 60 mg, about 60 mg and about 70 mg, about 70 mg and about 80 mg, about 80 mg and about 90 mg, about 90 mg and about 100 mg, about 100 mg and about 110 mg, about 110 mg and about 120 mg, about 120 mg and about 130 mg, about 130 mg and about 140 mg, about 140 mg and about 150 mg, about 150 mg and about 160 mg, about 160 mg and about 170 mg, about 170 mg and about 180 mg, about 180 mg and about 190 mg, or about 190 mg and about 200 mg of glutamic acid. In some embodiments, each gram of the nutritional supplement comprises about 174 mg of glutamic acid.

In some embodiments, the nutritional supplement comprises greater than about 20 mg of glycine per gram of rice protein isolate. In some embodiments, the nutritional supplement comprises greater than about 80, 70, 60, 50, 40, 30, 20, or 10 mg of glycine per gram of rice protein isolate. In some embodiments, each gram of the rice protein isolate comprises between about 0 mg and about 10 mg, about 10 mg and about 20 mg, about 20 mg and about 30 mg, about 30 mg and about 40 mg, about 40 mg and about 50 mg, or about 50 mg and about 60 mg of glycine. In some embodiments, each gram of the nutritional supplement comprises about 43 mg of glycine.

In some embodiments, the nutritional supplement comprises greater than about 20 mg of histidine per gram of rice protein isolate. In some embodiments, the nutritional supplement comprises greater than about 40, 30, 20, 10 mg or 5 mg of histidine per gram of rice protein isolate. In some embodiments, each gram of the rice protein isolate comprises between about 0 mg and about 5 mg, about 5 mg and about 15 mg, about 15 mg and about 25 mg, or about 25 mg and about 35 mg of histidine. In some embodiments, each gram of the nutritional supplement comprises about 22 mg of histidine.

In some embodiments, the nutritional supplement comprises greater than about 25 mg of methionine per gram of rice protein isolate. In some embodiments, the nutritional supplement comprises greater than about 40, 30, 20, or 10 mg of methionine per gram of rice protein isolate. In some embodiments, each gram of the rice protein isolate comprises between about 0 mg and about 5 mg, about 5 mg and about 15 mg, about 15 mg and about 25 mg, about 25 mg and about 35 mg, or about 35 mg and about 45 mg of methionine. In some embodiments, each gram of the nutritional supplement comprises about 28 mg of methionine.

In some embodiments, the nutritional supplement comprises greater than about 35 mg of phenylalanine per gram of rice protein isolate. In some embodiments, the nutritional supplement comprises greater than about 80, 70, 60, 50, 40, 30, 20, or 10 mg of phenylalanine per gram of rice protein isolate. In some embodiments, each gram of the rice protein isolate comprises between about 0 mg and about 10 mg, about 10 mg and about 20 mg, about 20 mg and about 30 mg, about 30 mg and about 40 mg, about 40 mg and about 50 mg, about 50 mg and about 60 mg, or about 60 mg and about 70 mg of phenylalanine. In some embodiments, each gram of the nutritional supplement comprises about 53 mg of phenylalanine.

In some embodiments, the nutritional supplement comprises less than about 60 mg of proline per gram of rice protein isolate. In some embodiments, the nutritional supplement comprises less than about 80, 70, 60, 50, 40, 30, 20, or 10 mg of proline per gram of rice protein isolate. In some embodiments, each gram of the rice protein isolate comprises between about 0 mg and about 10 mg, about 10 mg and about 20 mg, about 20 mg and about 30 mg, about 30 mg and about 40 mg, about 40 mg and about 50 mg, about 50 mg and about 60 mg, or about 60 mg and about 70 mg of proline. In some embodiments, each gram of the nutritional supplement comprises about 45 mg of proline.

In some embodiments, the nutritional supplement comprises less than about 50 mg of serine per gram of rice protein isolate. In some embodiments, the nutritional supplement comprises less than about 80, 70, 60, 50, 40, 30, 20, or 10 mg of serine per gram of rice protein isolate. In some embodiments, each gram of the rice protein isolate comprises between about 0 mg and about 5 mg, about 5 mg and about 15 mg, about 15 mg and about 25 mg, about 25 mg and about 35 mg, about 35 mg and about 45 mg, about 45 and about 55 mg, about 55 mg and about 65 mg of serine. In some embodiments, each gram of the nutritional supplement comprises about 49 mg of serine.

In some embodiments, the nutritional supplement comprises less than about 20 mg of tryptophan per gram of rice protein isolate. In some embodiments, the nutritional supplement comprises less than about 60, 50, 40, 30, 20, or 10 mg of tryptophan per gram of rice protein isolate. In some embodiments, each gram of the rice protein isolate comprises between about 0 mg and about 10 mg, about 10 mg and about 20 mg, about 20 mg and about 30 mg of tryptophan. In some embodiments, each gram of the nutritional supplement comprises about 14 mg of tryptophan.

In some embodiments, the nutritional supplement comprises greater than about 35 mg of tyrosine per gram of rice protein isolate. In some embodiments, the nutritional supplement comprises greater than about 80, 70, 60, 50, 40, 30, 20, 10 or 5 mg of tyrosine per gram of rice protein isolate. In some embodiments, each gram of the rice protein isolate comprises between about 0 mg and about 5 mg, about 5 mg and about 15 mg, about 15 and about 25 mg, about 25 mg and about 35 mg, about 35 mg and about 45 mg, about 45 mg and about 55 mg, or about 55 mg and about 65 mg of tyrosine. In some embodiments, each gram of the nutritional supplement comprises about 47 mg of tyrosine.

In some embodiments of the nutritional supplement, each gram of the rice protein isolate comprises between about 50 mg and about 60 mg alanine, between about 70 mg and 80 mg arginine, between about 80 mg and about 90 mg aspartic acid, between about 15 mg and about 25 mg cysteine, between about 170 mg and 180 mg of glutamic acid, about 40 mg and about 50 mg glycine, between about 15 mg and about 25 mg histidine, between about 35 mg about 45 mg isoleucine, between about 75 mg and about 95 mg of leucine, between about 25 mg and about 55 mg lysine, between about 25 mg and about 35 mg of methionine, between about 50 mg and about 60 mg phenylalanine, between about 40 mg and about 50 mg proline, between about 45 mg and about 55 mg serine, between about 30 mg and about 40 mg threonine, between about 10 mg and about 20 mg tryptophan, between about 45 mg and about 55 mg tyrosine, and between about 55 mg and about 65 mg of valine.

In some embodiments of the nutritional supplement, each gram of the rice protein isolate comprises about 54 mg alanine, about 77 mg arginine, about 87 mg aspartic acid, about 21 mg cysteine, about 174 mg glutamic acid, about 43 mg glycine, about 22 mg histidine, about 41 mg isoleucine, about 80 mg leucine, about 31 mg lysine, about 28 mg methionine, about 53 mg phenylalanine, about 45 mg proline, about 49 mg serine, about 35 mg threonine, about 14 mg tryptophan, about 47 mg tyrosine, and about 58 mg valine.

In some embodiments, each gram of the nutritional supplement comprises between about 30 mg and about 50 mg alanine. In some embodiments, each gram of the nutritional supplement comprises between about 40 mg and 65 mg arginine. In some embodiments, each gram of the nutritional supplement comprises between about 60 mg and about 85 mg aspartic acid. In some embodiments, each gram of the nutritional supplement comprises between about 10 mg and about 25 mg cysteine. In some embodiments, each gram of the nutritional supplement comprises between about 115 mg and 160 mg of glutamic acid. In some embodiments, each gram of the nutritional supplement comprises about 15 mg and about 35 mg glycine. In some embodiments, each gram of the nutritional supplement comprises between about 10 mg and about 25 mg histidine. In some embodiments, each gram of the nutritional supplement comprises between about 35 mg and about 55 mg isoleucine. In some embodiments, each gram of the nutritional supplement comprises between about 60 mg and about 85 mg of leucine. In some embodiments, each gram of the nutritional supplement comprises between about 30 mg and about 50 mg lysine. In some embodiments, each gram of the nutritional supplement comprises between about 10 mg and about 25 mg of methionine. In some embodiments, each gram of the nutritional supplement comprises between about 25 mg and about 45 mg phenylalanine. In some embodiments, each gram of the nutritional supplement comprises between about 40 mg and about 60 mg proline. In some embodiments, each gram of the nutritional supplement comprises between about 30 mg and about 50 mg serine. In some embodiments, each gram of the nutritional supplement comprises between about 30 mg and about 50 mg threonine. In some embodiments, each gram of the nutritional supplement comprises between about 5 mg and about 20 mg tryptophan. In some embodiments, each gram of the nutritional supplement comprises between about 20 mg and about 40 mg tyrosine. In some embodiments, each gram of the nutritional supplement comprises between about 35 mg and about 60 mg of valine.

In some embodiments, each gram of the nutritional supplement comprises between about 30 mg and about 50 mg alanine, between about 40 mg and about 65 mg arginine, between about 60 mg and about 85 mg aspartic acid, between about 10 mg and about 25 mg cysteine, between about 115 mg and 160 mg of glutamic acid, about 15 mg and about 35 mg glycine, between about 10 mg and about 25 mg histidine, between about 35 mg about 55 mg isoleucine, between about 60 mg and about 85 mg of leucine, between about 30 mg and about 50 mg lysine, between about 10 mg and about 25 mg of methionine, between about 25 mg and about 45 mg phenylalanine, between about 40 mg and about 60 mg proline, between about 30 mg and about 50 mg serine, between about 30 mg and about 50 mg threonine, between about 5 mg and about 20 mg tryptophan, between about 20 mg and about 40 mg tyrosine, and between about 35 mg and about 60 mg of valine.

In some embodiments, each gram of the nutritional supplement comprises about 37.9 mg alanine. In some embodiments, each gram of the nutritional supplement comprises about 52.8 mg arginine. In some embodiments, each gram of the nutritional supplement comprises about 70.5 mg aspartic acid. In some embodiments, each gram of the nutritional supplement comprises about 18.8 mg cysteine. In some embodiments, each gram of the nutritional supplement comprises about 133.3 mg glutamic acid. In some embodiments, each gram of the nutritional supplement comprises about 24.4 mg glycine. In some embodiments, each gram of the nutritional supplement comprises about 17.4 mg histidine. In some embodiments, each gram of the nutritional supplement comprises about 45.1 mg isoleucine. In some embodiments, each gram of the nutritional supplement comprises about 70.5 mg leucine. In some embodiments, each gram of the nutritional supplement comprises about 39.6 mg lysine. In some embodiments, each gram of the nutritional supplement comprises about 17.8 mg methionine. In some embodiments, each gram of the nutritional supplement comprises about 33.9 mg phenylalanine. In some embodiments, each gram of the nutritional supplement comprises about 47.2 mg proline. In some embodiments, each gram of the nutritional supplement comprises about 38.1 mg serine. In some embodiments, each gram of the nutritional supplement comprises about 36.8 mg threonine. In some embodiments, each gram of the nutritional supplement comprises about 12.1 mg tryptophan. In some embodiments, each gram of the nutritional supplement comprises about 31.7 mg tyrosine. In some embodiments, each gram of the nutritional supplement comprises about 46.6 mg valine.

In some embodiments, each gram of the rice protein isolate comprises about 37.9 mg alanine, about 52.8 mg arginine, about 70.5 mg aspartic acid, about 18.8 mg cysteine, about 133.3 mg glutamic acid, about 24.4 mg glycine, about 17.4 mg histidine, about 45.1 mg isoleucine, about 70.5 mg leucine, about 39.6 mg lysine, about 17.8 mg methionine, about 33.9 mg phenylalanine, about 47.2 mg proline, about 38.1 mg serine, about 36.8 mg threonine, about 12.1 mg tryptophan, about 31.7 mg tyrosine, and about 46.6 mg valine.

In some embodiments, each gram of the nutritional supplement comprises one or more of about 34.6 mg alanine, about 48.1 mg arginine, about 64.2 mg aspartic acid, about 16.9 mg cysteine, about 121.5 mg glutamic acid, about 22.2 mg glycine, about 15.8 mg histidine, about 41.2 mg isoleucine, about 64.2 mg leucine, about 36.1 mg lysine, about 16.2 mg methionine, about 30.9 mg phenylalanine, about 43.1 mg proline, about 34.7 mg serine, about 33.5 mg threonine, about 11.0 mg tryptophan, about 28.9 mg tyrosine, and about 42.5 mg valine.

In some embodiments, each gram of the rice protein isolate comprises about 34.6 mg alanine, about 48.1 mg arginine, about 64.2 mg aspartic acid, about 16.9 mg cysteine, about 121.5 mg glutamic acid, about 22.2 mg glycine, about 15.8 mg histidine, about 41.2 mg isoleucine, about 64.2 mg leucine, about 36.1 mg lysine, about 16.2 mg methionine, about 30.9 mg phenylalanine, about 43.1 mg proline, about 34.7 mg serine, about 33.5 mg threonine, about 11.0 mg tryptophan, about 28.9 mg tyrosine, and about 42.5 mg valine.

In some embodiments, each gram of the nutritional supplement comprises one or more of about 43.6 mg alanine, about 60.6 mg arginine, about 80.9 mg aspartic acid, about 21.3 mg cysteine, about 153 mg glutamic acid, about 28 mg glycine, about 19.9 mg histidine, about 51.9 mg isoleucine, about 80.9 mg leucine, about 45.5 mg lysine, about 20.4 mg methionine, about 39.0 mg phenylalanine, about 54.2 mg proline, about 43.7 mg serine, about 42.2 mg threonine, about 13.9 mg tryptophan, about 36.4 mg tyrosine, and about 53.5 mg valine.

In some embodiments, each gram of the rice protein isolate comprises about 43.6 mg alanine, about 60.6 mg arginine, about 80.9 mg aspartic acid, about 21.3 mg cysteine, about 153 mg glutamic acid, about 28 mg glycine, about 19.9 mg histidine, about 51.9 mg isoleucine, about 80.9 mg leucine, about 45.5 mg lysine, about 20.4 mg methionine, about 39.0 mg phenylalanine, about 54.2 mg proline, about 43.7 mg serine, about 42.2 mg threonine, about 13.9 mg tryptophan, about 36.4 mg tyrosine, and about 53.5 mg valine.

In some embodiments, besides the rice protein isolate, the nutritional supplement further comprises one or more of organic sprouted whole grain brown rice syrup solids, organic flavor, organic guar gum, organic gum arabic, organic stevia, sea salt, and organic sunflower oil.

In some embodiments, the nutritional supplement comprises rice protein isolate, organic flavor, organic guar gum, organic gum arabic, organic stevia, sea salt, and organic sunflower oil.

In some embodiments, the only source of protein in the nutritional supplement consists of rice protein isolate.

Methods

Some embodiments provide methods of improving the results of exercise training by providing a subject with any one of the nutritional supplements described above. It has been found that, surprisingly, the nutritional supplements comprising rice protein isolates described herein provide sufficient amino acid profiles for sustained improvements in exercise training outcomes and nutritional supplementation outcomes. Exercise training with ingestion of the nutritional supplements described above before, during, or after exercise training results in one or more of increased muscle mass, increased strength, increased power, increased endurance, increased VO2 max, increased cardiovascular endurance, increased respiratory endurance, increased stamina, increased lean body mass, improved body composition, or decreased fat. Some embodiments provide the supplementation of a diet of a subject, comprising providing the nutritional supplements described above to a subject, wherein the subject is a newborn, infant, toddler, child, adolescent, adult, or a geriatric individual, wherein ingestion of an effective amount of the nutritional supplement by the subject results in one or more of weight gain, weight maintenance, growth, muscle growth, muscle maintenance, decreased muscle loss, improved recovery after exercise training, faster recovery after exercise training, decreased muscle soreness associated with exercise training, or maintaining nitrogen balance. In some embodiments, by supplementing the diet of a subject, improvements in results of exercise training can be achieved along with improvements in the ability to perform day-to-day activities (e.g. climbing stairs, getting out of a chair, walking).

In some embodiments, the method of improving a result of exercise training in a subject comprises providing a nutritional supplement comprising a rice protein isolate to the subject, wherein ingestion of an effective amount of the nutritional supplement by the subject before, during, and/or after exercise training results in one or more of increased muscle mass, increased strength, increased power, increased endurance, increased VO2 max, increased cardiovascular endurance, increased respiratory endurance, increased stamina, increased lean body mass, improved body composition, or decreased fat.

In some embodiments of the method, the improved result of exercise training is increased skeletal muscle hypertrophy. In some embodiments of the method, the improved result of exercise training is an increase in strength. In some embodiments of the method, the improved result of exercise training is an increase in power. In some embodiments of the method, the improved result of exercise training is improved body composition. In some embodiments of the method, the improved result of exercise training is an increase VO2 max. In some embodiments of the method, the improved result of exercise training is an increase in exercise duration and/or exercise performance.

In some embodiments, supplementation using the rice protein isolates described herein results in muscle mass, strength, power, endurance, VO2 max, cardiovascular endurance, respiratory endurance, stamina, lean body mass, body composition, and/or fat composition changes in a subject that are comparable to (e.g., not statistically different from supplementation with whey protein). In some embodiments, the administration of the nutritional supplement before, during, and/or after exercise training results in quicker recovery and/or less perceived soreness after exercise training in a subject that is comparable to and/or has a statistically insignificant difference to supplementation using whey protein (wherein the rice protein isolate and whey protein isolate are isonitrogenous, isocaloric, and/or macronutrient ratio matched with one another).

In some embodiments, the method of providing a nutritional supplement comprising a rice protein isolate to a subject before, during, and/or after exercise training results in a muscle mass increase ranging from about 0.5% to about 1.5%, about 1.5% to about 2.5%, about 2.5% to about 5.0%, or greater than 5.0% after a four week period of using the supplement. In some embodiments, the method of providing a nutritional supplement comprising a rice protein isolate to a subject before, during, and/or after exercise training results in a muscle mass increase ranging from about 0.5% to about 1.5%, about 1.5% to about 2.5%, about 2.5% to about 5.0%, about 5.0% to about 7.5%, about 7.5% to about 10.0%, or greater than 10.0% after an eight week period of using the supplement.

In some embodiments, the method of providing a nutritional supplement comprising a rice protein isolate to a subject before, during, and/or after exercise training results in an increase in strength (as measured by the improvement in amount of weight lifted performing a one rep maximum lift) ranging from about 0.5% to about 2.5%, about 2.5% to about 5.0%, about 5.0% to about 10.0%, 10.0% to about 20%, or greater than 20.0% after a four week period of using the supplement. In some embodiments, the method of providing a nutritional supplement comprising a rice protein isolate to a subject before, during, and/or after exercise training results in an increase in strength ranging from about 0.5% to about 2.5%, about 2.5% to about 5.0%, about 5.0% to about 10.0%, about 10.0% to about 20.0%, about 20.0% to about 30.0%, or greater than 30.0% after an eight week period of using the supplement.

In some embodiments, the method of providing a nutritional supplement comprising a rice protein isolate to a subject before, during, and/or after exercise training results in an increase in power (as measured by during a maximal cycling ergometry test, as described below) ranging from about 0.5% to about 2.5%, about 2.5% to about 5.0%, about 5.0% to about 10.0%, 10.0% to about 20%, or greater than 20.0% after a four week period of using the supplement. In some embodiments, the method of providing a nutritional supplement comprising a rice protein isolate to a subject before, during, and/or after exercise training results in an increase in strength ranging from about 0.5% to about 2.5%, about 2.5% to about 5.0%, about 5.0% to about 10.0%, about 10.0% to about 20.0%, about 20.0% to about 30.0%, or greater than 30.0% after an eight week period of using the supplement.

In some embodiments, the method of providing a nutritional supplement comprising a rice protein isolate to a subject before, during, and/or after exercise training results in a VO2 max increase ranging from about 0.5% to about 1.5%, about 1.5% to about 2.5%, about 2.5% to about 5.0%, or greater than 5.0% after a four week period of using the supplement. In some embodiments, the method of providing a nutritional supplement comprising a rice protein isolate to a subject before, during, and/or after exercise training results in a VO2 max increase ranging from about 0.5% to about 1.5%, about 1.5% to about 2.5%, about 2.5% to about 5.0%, about 5.0% to about 7.5%, about 7.5% to about 10.0%, or greater than 10.0% after an eight week period of using the supplement.

In some embodiments, the method of providing a nutritional supplement comprising a rice protein isolate to a subject before, during, and/or after exercise training results in a lean body mass increase ranging from about 0.5% to about 1.5%, about 1.5% to about 2.5%, about 2.5% to about 5.0%, or greater than 5.0% after a four week period of using the supplement. In some embodiments, the method of providing a nutritional supplement comprising a rice protein isolate to a subject before, during, and/or after exercise training results in a muscle mass increase ranging from about 0.5% to about 1.5%, about 1.5% to about 2.5%, about 2.5% to about 5.0%, about 5.0% to about 7.5%, about 7.5% to about 10.0%, or greater than 10.0% after an eight week period of using the supplement.

In some embodiments, the method of providing a nutritional supplement comprising a rice protein isolate to a subject before, during, and/or after exercise training results in a body fat decrease ranging from about 0.5% to about 1.5%, about 1.5% to about 2.5%, about 2.5% to about 5.0%, or greater than 5.0% after a four week period of using the supplement. In some embodiments, the method of providing a nutritional supplement comprising a rice protein isolate to a subject before, during, and/or after exercise training results in a body fat decrease ranging from about 0.5% to about 1.5%, about 1.5% to about 2.5%, about 2.5% to about 5.0%, about 5.0% to about 7.5%, about 7.5% to about 10.0%, or greater than 10.0% after an eight week period of using the supplement.

Some embodiments pertain to methods of supplementing the diet of a subject. In some embodiments, the diet supplementation involves providing nutritional supplementation for weight gain, weight maintenance, decreased weight loss, growth, muscle growth, muscle maintenance, and/or decreased muscle loss in newborn or infant subjects. In some instances, newborns and/or infants may have reactions (e.g. allergic reactions) to breast milk, whey, or soy based proteins. In such instances, rice protein may be provided as an alternative protein source. In some embodiments, the method of providing nutritional supplementation to a newborn or infant subject comprises providing a nutritional supplement comprising a rice protein isolate to the subject, wherein ingestion of an effective amount of the nutritional supplement by the subject between meals, as a meal replacement, or combinations thereof results in one or more of weight gain, weight maintenance, body growth, muscle growth, maintenance of muscle mass, or fat gain.

Some embodiments pertain to methods of providing nutritional supplementation for one or more of weight gain, weight maintenance, decreased weight loss, growth, muscle growth, muscle maintenance, or decreased muscle loss in one or more of a newborn, infant, toddler, child, adolescent, adult, or geriatric subject. In some embodiments, the method of providing nutritional supplementation to one or more of a newborn, infant, toddler, child, adolescent, adult, or geriatric subject comprises providing a nutritional supplement comprising a rice protein isolate to the subject, wherein ingestion of an effective amount of the nutritional supplement by the subject between meals, as a meal replacement, or combinations thereof results in one or more of weight gain, weight maintenance, growth, muscle growth, muscle maintenance, decreased muscle loss, improved recovery after exercise training, decreased recovery time associated with exercise training, decreased muscle soreness associated with exercise training, or maintained nitrogen balance. Nitrogen balance maintenance can be a measure of muscle amounts in the body.

Some embodiments provide methods of supplementing the diet of a subject, comprising providing any of the nutritional supplements described above to a subject, wherein the subject is a newborn, infant, toddler, child, adolescent, adult, or a geriatric individual, wherein ingestion of an effective amount of the nutritional supplement by the subject results in at least one of weight gain, weight maintenance, growth, muscle growth, muscle maintenance, decreased muscle loss, improved recovery after exercise training, decreased recovery time associated with exercise training, decreased muscle soreness associated with exercise training, or nitrogen balance maintenance.

In some embodiments of the methods described above, servings of the nutritional supplement comprising rice protein isolate are provided to the subject for ingestion once, twice, three times, four times, or five times, or more than five times daily. In some embodiments, the method the nutritional supplement is provided for ingestion on nonconsecutive days (e.g one time per week, two times per week, three times per week, four times per week, five times per week, or six times per week) or by a schedule determined by a physician.

In some embodiments, the effective amount of nutritional supplement is a serving of dry nutritional supplement weighing between about 1 g and about 10 g, about 10 g and about 20 g, about 20 g and about 30 g, about 30 g and about 40 g, about 40 g and about 50 g, about 50 g and about 60 g, or over 60 g. The dry powder can be mixed with any suitable liquid (e.g. water, milk, juice) to form a solution or mixture that can be ingested. The dry powder could further be added to other food sources (e.g. addition to food recipes) or formulated as solid products (e.g. a bar, a gummy).

In some embodiments, the percentage by weight of rice protein isolate in the dry nutritional supplement is about 60% to about 70%, about 70% to about 80%, about 80% to about 90%, above 90%, values in between the aforementioned values, and otherwise.

In some embodiments of the methods described above, the nutritional supplement comprises less than about 95 mg of leucine per gram of rice protein isolate. In some embodiments, the nutritional supplement comprises less than about 55 mg of lysine per gram of rice protein isolate. In some embodiments of the method, the provided nutritional supplement comprises less than about 50 mg of isoleucine per gram of rice protein isolate. In some embodiments, the nutritional supplement comprises less than about 60 mg of valine per gram of rice protein isolate.

In some embodiments of the method, the provided nutritional supplement comprises between about 50 mg and about 60 mg alanine, between about 70 mg and 80 mg arginine, between about 80 mg and about 90 mg aspartic acid, between about 15 mg and about 25 mg cysteine, between about 170 mg and 180 mg of glutamic acid, about 40 mg and about 50 mg glycine, between about 15 mg and about 25 mg histidine, between about 35 mg about 45 mg isoleucine, between about 75 mg and about 95 mg of leucine, between about 25 mg and about 55 mg lysine, between about 25 mg and about 35 mg of methionine, between about 50 mg and about 60 mg phenylalanine, between about 40 and about 50 mg proline, between about 45 mg and about 55 mg serine, between about 30 mg and about 40 mg threonine, between about 10 mg and about 20 mg tryptophan, between about 45 mg and about 55 mg tyrosine, and between about 55 mg and about 65 mg of valine per gram of rice protein isolate.

In some embodiments of the method, the provided nutritional supplement comprises about 54 mg alanine, about 77 mg arginine, about 87 mg aspartic acid, about 21 mg cysteine, about 174 mg glutamic acid, about 43 mg glycine, about 22 mg histidine, about 41 mg isoleucine, about 80 mg leucine, about 31 mg lysine, about 28 mg methionine, about 53 mg phenylalanine, about 45 mg proline, about 49 mg serine, about 35 mg threonine, about 14 mg tryptophan, about 47 mg tyrosine, and about 58 mg valine per gram of rice protein isolate.

Some embodiments involve decreasing the Tmax of leucine in a subject by providing the nutritional supplements described above for ingestion by a subject. In some embodiments, the Tmax for leucine achieved using the nutritional supplements described above is less than about 30, 40, 50, 60, 70, 80, or 90 minutes. In some embodiments, the Tmax for leucine achieved using the nutritional supplements described above is between about 1 minute and about 30 minutes, about 30 minutes and about 40 minutes, about 40 minutes and about 50 minutes, about 50 minutes and about 60 minutes, about 60 minutes and about 70 minutes, about 70 minutes and about 80 minutes, about 80 minutes to about 90 minutes, or over 90 minutes. In some embodiments, the Tmax for leucine achieved using the nutritional supplements described above is between about 1 minute and about 90 minutes, about 30 minutes and about 90 minutes, about 40 minutes and about 80 minutes, or about 50 minutes and about 70 minutes. In some embodiments, the Tmax for leucine using the nutritional supplements described above is faster than the Tmax using a whey protein isolate.

EXAMPLES

Example 1

The purpose of this study was to investigate the effects of doses of rice protein compared to equal doses of whey protein on skeletal muscle hypertrophy, lean body mass, strength and power when given following 8 weeks of periodized RT in those individuals with previous RT experience.

Experimental Design

The study consisted of a randomized, double blind protocol consisting of individuals given either 48 grams of rice or 48 grams of whey protein isolate following an acute resistance exercise bout (Phase 1) and following each session during an 8 week periodized training protocol (Phase 2). Phase 1 of the study investigated the effects of protein sources on recovery 48 hours following a high volume, hypertrophy oriented resistance-training session. Phase two occurred for the remaining eight-week RT protocol, which consisted of training each muscle group twice per week using a non-linear periodized RT model. Direct ultrasound determined muscle mass, dual emissions x-ray absorptiometery (DXA) determined body composition, maximal strength, and power were assessed collectively at the end of weeks 0, 4, and 8.

Phase 1 Resistance Training Protocol

All subjects participated in a high volume resistance training session consisting of 3 sets of leg press, bench press, and military press, pull-ups, bent over rows, barbell curls and extensions (shown below). Immediately following the workout, subjects consumed 48 grams of RPI or WPI respectively. Immediately prior to the exercise session and 48 hours post exercise, soreness, perceived readiness to train, and perceived recovery scale (PRS) measurements were taken. Soreness was measured on a visual analogue scale ranging from 0-10. With zero representing no soreness in the muscles at all, and 10 representing the worst muscle soreness ever experienced. PRS consists of values between 0-10, with 0-2 being very poorly recovered with anticipated declines in performance, 4-6 being low to moderately recovered with expected similar performance, and 8-10 representing high perceived recovery with expected increases in performance. Perceived readiness indicates how ready the subject felt they were to train. In this scale a 10 is the most ready an individual could be to train, while a 0 indicates the subject feels they are not ready at all to train.

Resistance Training Protocol

The program was designed to train all major muscle groups using mostly compound movements for the upper and lower body (Table 1). The programmed, non-linear training split was divided into hypertrophy days consisting of 8-12 RM loads for 3 sets, with 60-120 seconds rest and strength days consisting of 2 to 5 RM loads for 3 sets for all exercises except the leg press and bench press which received 5 total sets. Weights were progressively increased by 2-5% when the prescribed repetitions could be completed. All training sessions were closely monitored by the researchers to ensure effort and intensity were maximal each training session.

TABLE 1

| Monday | Tuesday | Wednesday | Thursday | Friday |
|---|---|---|---|---|
| Hypertrophy (leg & chest) | | Hypertrophy (back & delts) | | Strength |
| Leg Press | | Pull-ups | | Leg Press |
| Leg Curl | | 90° Bent Rows | | Bench Press |
| Leg Extension | | Shrugs | | Leg Extension |
| Hyperextension | | Shoulder Press | | Close Grip Bench Press |
| Bench Press | | Lateral Raise | | |
| Dumbbell Incline Bench Press | | Reverse Laterals | | |
| Close Grip Bench Press | | Bicep curls | | |
| Skullcrushers | | | | |

Strength, Power, Body Composition and Skeletal Muscle Hypertrophy Testing

Strength was assessed via 1-RM testing of the leg press and bench press. Each lift was deemed successful as described by International Powerlifting Federation rules.

Body composition (lean body mass, fat mass, and total mass) was determined on a Lunar Prodigy DXA apparatus (software version, enCORE 2008, Madison, Wis., U.S.A.). Skeletal muscle hypertrophy was determined via changes in ultrasonography determined combined muscle thickness of the biceps brachii and vastus lateralis (VL) and vastus intermedius (VI) muscles (General Electric Medical Systems, Milwaukee, Wis., USA).

Power was assessed during a maximal cycling ergometry test. During the cycling test, the volunteer was instructed to cycle against a predetermined resistance (7.5% of body weight) as fast as possible for 10 seconds. The saddle height was adjusted to the individual's height to produce a 5-100 knee flexion while the foot was in the low position of the central void. A standardized verbal stimulus was provided to the subjects. Power output was recorded in real time by a computer connected to the Monark standard cycle ergometer (Monark model 894e, Vansbro, Sweden) during the 10-second sprint test. Peak power (PP) was recorded using Monark Anaerobic test software (Monark Anaerobic Wingate Software, Version 1.0, Monark, Vansbro, Sweden). From completion of wingate tests performed over several days, interclass correlation coefficient for peak power was 0.96.

Supplementation and Diet Control

Two weeks prior to and throughout the study, subjects were placed on a diet consisting of 25% protein, 50% carbohydrates, and 25% fat by a registered dietician who specialized in sport nutrition. Subjects met as a group with the dietitian, and they were given individual meal plans at the beginning of the study. Daily total of calories were determined by the harris benedict equation and tracked by weekly logs to ensure compliance. The protein supplement was administered under supervision of a laboratory assistant following resistance training, and it consisted of either 48 g of whey protein isolate (Nutra Bio Whey Protein Isolate (Dutch Chocolate), Middlesex, N.J.; FIG. 1B) or 48 g of rice protein isolate (Growing Naturals Rice Protein Isolate (Chocolate Power) made with Oryzatein® rice protein, Axiom Foods, Oro Valley, Ariz.; FIG. 1A) dissolved in 500 ml of water. The amino acid profile of the study material was analyzed by an independent analytical laboratory (Eurofins Analytical Laboratories, Metairie, La.) and is displayed in Table 2. Both the whey protein supplement and rice protein supplement were isonitrogenous, isocaloric, and macronutrient ratio matched.

TABLE 2

| Amino Acid | Whey Protein Isolate (mg/g of protein) | Rice Protein Isolate (mg/g of protein) |
|---|---|---|
| Alanine | 54 | 54 |
| Arginine | 23 | 77 |
| Aspartic Acid | 118 | 87 |
| Cystine | 25 | 21 |
| Glutamic Acid | 191 | 174 |
| Glycine | 19 | 43 |
| Histidine | 18 | 22 |
| Isoleucine | 70 | 41 |
| Leucine | 115 | 80 |
| Lysine | 101 | 31 |
| Methionine | 23 | 28 |
| Phenylalanine | 33 | 53 |
| Proline | 64 | 45 |
| Serine | 52 | 49 |
| Threonine | 76 | 35 |
| Tryptophan | 22 | 14 |
| Tyrosine | 31 | 47 |
| Valine | 64 | 58 |

All supplements were tested by HFL Sports Science prior to use to ensure no contamination with steroids or stimulants according to ISO 17025 accredited tests.

Statistics

An ANOVA model was used to measure group, time, and group by time interactions for both phase 1 and 2. If any main effects were observed, a Tukey post-hoc was employed to locate where differences occurred. All statistics were run using Statistica software (Statsoft, 2011).

Results

Phase 1

Figure 2A:
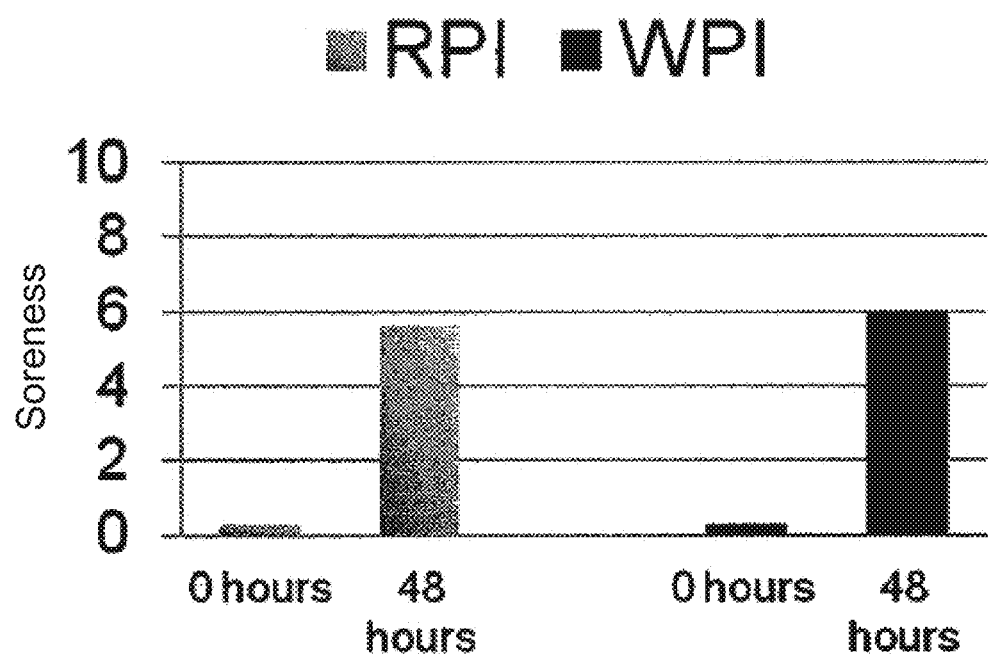
FIGS. 2A-2F depict test results for subjects using rice protein isolate or whey protein isolate for supplementation after exercise training.
Figure 2B:
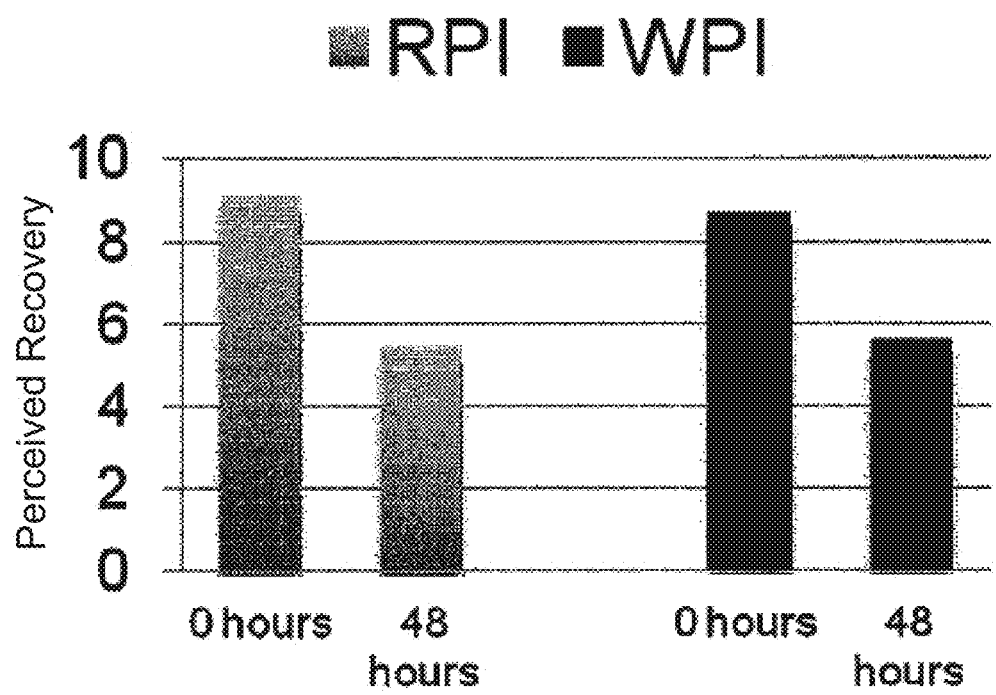
Figure 2:
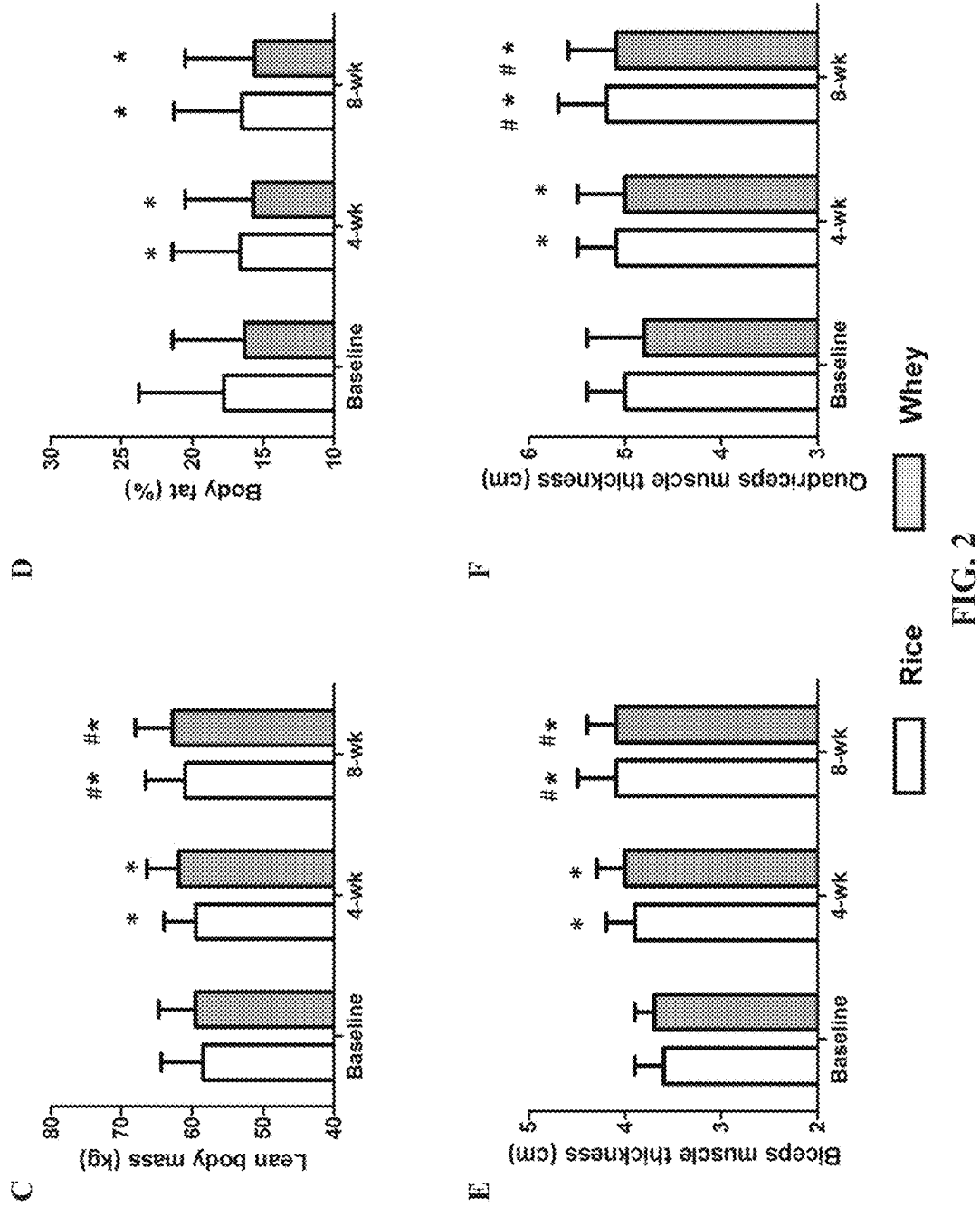

No differences existed between groups at baseline for any measure. There were no differences between the total amounts of weight lifted by the RPI (12296.3±2412.6 kg) or WPI (11831.6±2611.3 kg) group during the resistance training session. There was a significant time effect ($p<0.05$) for soreness, which increased in both the RPI (0.3±0.6 to 5.6±2.2) and WPI (0.3±0.5 to 6.0±1.9) groups, with no differences between groups (no condition X time effect; FIG. 2A). There was a significant time effect ($p<0.05$) for PRS, which decreased in both the RPI (9.1±1.5 to 5.45±1.5) and WPI (8.7±2.6 to 5.6±1.4) groups, with no differences between groups (no condition X time effect; FIG. 2B). There were no significant time or condition x time effects for perceived readiness to train, indicating that the subject's perceived readiness had recovered within 48 hours. Rice protein was as effective as whey protein in recovery after resistance training.

Phase 2

There was a significant time effect ($p<0.01$) for lean body mass, which increased in both the rice (58.5±5.5 (baseline) to 59.5±4.5 (week 4) to 61.0±5.6 kg (week 8)) and whey protein (59.6±5.2 to 61.9±4.5 to 62.8±5.2 kg) conditions, with no differences between conditions (no condition X time effect). There was a significant time effect for body fat ($p<0.05$), which decreased in both conditions, 17.8±6.0 to 16.6±4.8 to 15.6±4.9 kg in the rice protein condition and 16.3±5.1 to 15.7±4.8 to 15.6±4.9 kg in the whey protein condition, from pre to post training, with no differences between conditions (no condition X time effect). There was a significant time effect for quadriceps and biceps thickness ($p<0.05$), which increased from pre to post training in the rice protein (5.0±0.4 to 5.1±0.4 to 5.2±0.5 cm and 3.6±0.3 to 3.9±0.3 to 4.1±0.4 cm, respectively) and whey protein (4.8±0.7 to 5.0±0.5 to 5.1±0.5 cm and 3.6±0.2 to 4.0±0.3 to 4.1±0.3 cm, respectively) conditions, with no differences between conditions (no condition X time effect). This data is displayed in FIG. 2C-F.

Figure 3A:
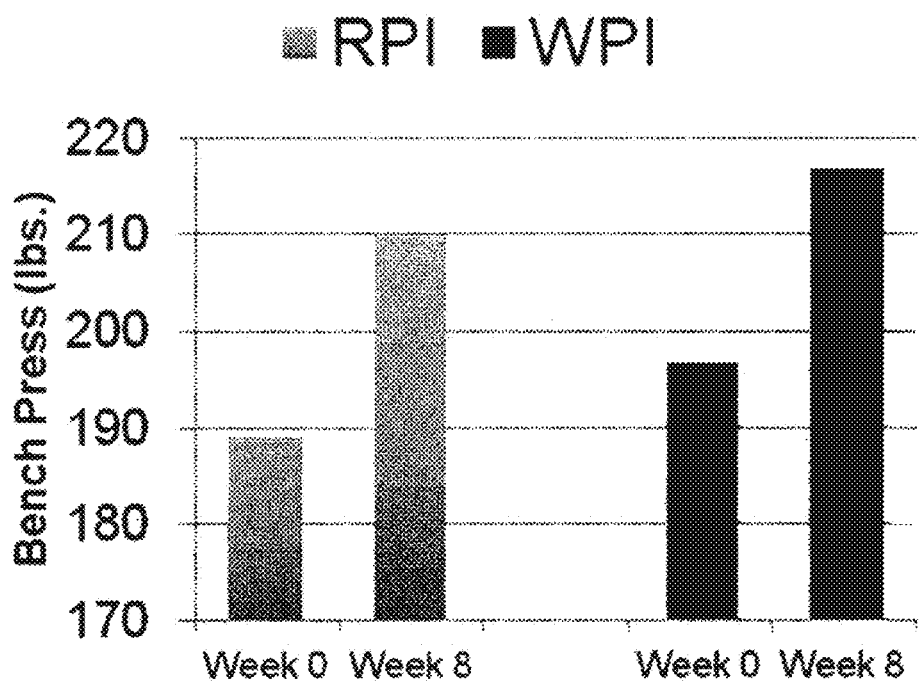
FIGS. 3A-3D depict test results for subjects using rice protein isolate or whey protein isolate for supplementation after exercise training.
Figure 3B:
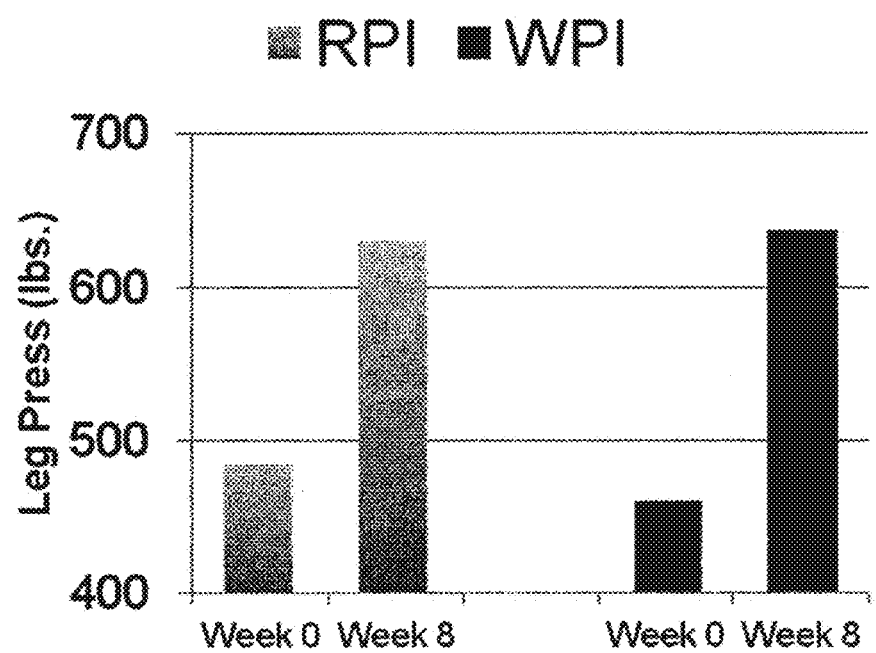
Figure 3C:
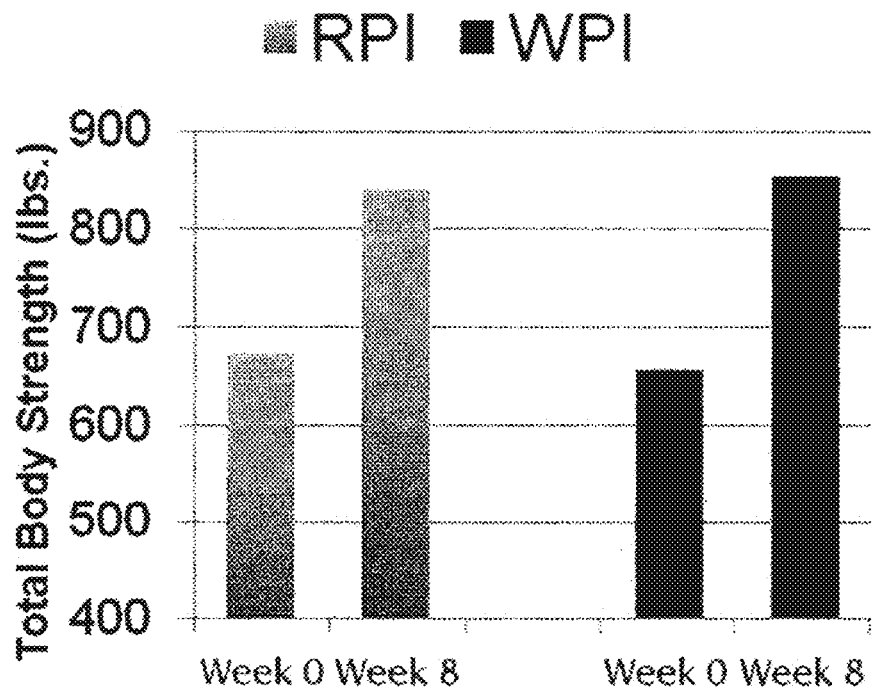
Figure 3D:
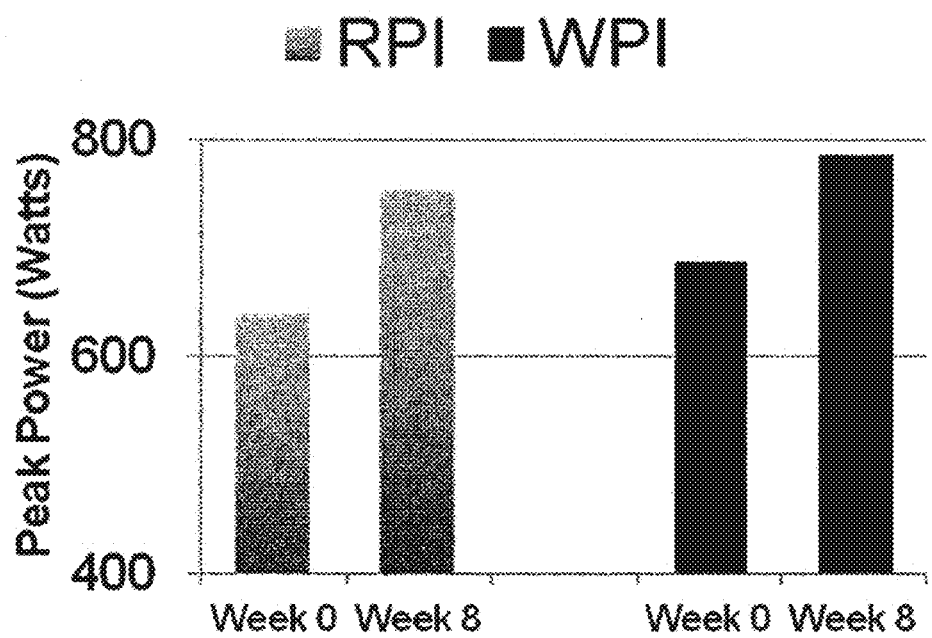

There was a significant time effect ($p<0.01$) for 1-RM bench press strength, which increased from baseline to week 8 in both the rice protein (85.9±20.5 to 95.5±21.4 kg) and whey protein (89.5±18.5 to 98.5±16.4 kg) conditions, with no differences between groups (no condition X time effect) (FIG. 3A). There was a significant time effect ($p<0.01$) for 1-RM leg press strength, which increased from baseline to week 8 in both the rice (220.0±38.5 to 286.8±37.2 kg) and whey (209.5±35.0 to 289.7±40.1 kg) conditions, with no differences between conditions (no condition X time effect) (FIG. 3B). Total body strength also showed no difference between conditions (FIG. 3C). There was a significant time effect for wingate peak power ($p<0.01$), which increased from baseline to week 8 in both the rice protein (638.4±117.2 to 753.9±115.6 watts) and whey protein (687.1±125.3 to 785.0±101.1 watts) conditions, with no differences between conditions (FIG. 3D). Performance data is displayed in Table 3.

TABLE 3

| | Baseline | Week 4 | Week 8 |
|---|---|---|---|
| Bench Press (kg) Rice Protein Isolate | 85.9 ± 20.5 | 91.6 ± 21.2 | 95.5 ± 21.4* |
| Bench Press (kg) Whey Protein Isolate | 89.5 ± 18.5 | 95.5 ± 17.8 | 98.5 ± 16.4* |
| Leg Press (kg) Rice Protein Isolate | 220.0 ± 38.5 | 266.4 ± 34.6 | 286.8 ± 37.2* |
| Leg Press (kg) Whey Protein Isolate | 209.5 ± 35 | 259.5 ± 39.6 | 289.7 ± 40.1 * |
| Peak Power (W) Rice Protein Isolate | 638.4 ± 117.2 | 692.5 ± 118.6 | 753.9 ± 115.6* |
| Peak Power (W) Whey Protein Isolate | 687.1 ± 125 | 740.8 ± 115.4 | 785.0 ± 101.1* |

Discussion

The purpose of this study was to investigate the effects of doses of rice protein compared to whey protein on acute recovery from high volume resistance training as well as skeletal muscle hypertrophy, lean body mass, strength and power when given following eight weeks of periodized RT. The novel finding in the present study is that no significant condition by time interactions were observed between the rice protein and whey protein supplements on short term recovery or training-induced adaptations. Our findings show that doses of rice protein (48 g) are, surprisingly, comparable to an equal dose of whey protein in its effects on lean mass and muscle responses after periodized RT. In other words, RPI supports changes in strength and body composition similarly to WPI.

Subjects were given either 48 g of protein in the form of a rice protein supplement or a whey protein supplement. Researchers conducted a dose response study of an egg protein supplement comparing 0 g, 5 g, 109, 20 g, and 40 g of egg protein delivered after a bout of exercise. After consumption of the supplement, MPS rates were monitored for four hours. Their results suggested that MPS was maximally stimulated with 20 g of egg protein, which contains 1.7 g of leucine. It was also observed that at double that dose (40 g, 3.4 g of leucine), no significant differences in MPS occurred.

Chronic free leucine supplementation alone did not improve lean body or muscle mass during resistance training in the elderly, whereas it was able to limit the weight loss induced by malnutrition. Leucine-rich amino acid mixture or proteins appeared more efficient than leucine alone to improve muscle mass and performance, suggesting the efficacy of leucine depends nevertheless on the presence of other amino acids. Small differences in protein digestion rates, differences in branched-chain amino acid content can impact the ability of the protein to maximize post exercise MPS. Available data on soy protein suggests that plant proteins generally might differ in their ability to support muscle protein accretion after resistance exercise.

For example, post exercise consumption of fat-free milk promotes greater hypertrophy during the early stages of resistance training in novice weightlifters when compared with isonitrogenous and isoenergetic fat-free soy protein. Researchers conducted experiments comparing milk protein, to soy protein, to a maltodextrin control in untrained individuals. In that study, 17.5 g of protein in the form of milk or soymilk was given immediately and one hour following exercise, while the control group received an isocaloric maltodextrin beverage. 17.5 g of protein from milk contains approximately 1.7 g of leucine, and 17.5 g of protein from soymilk would contain 1.4 g of leucine. Following a twelve week RT program, the milk protein group experienced greater increases in type II muscle fiber area. This study suggests that a moderate dose of milk protein increases lean mass to a greater extent than soy or a maltodextrin control when given following exercise. Soy proteins appear to support greater splanchnic rather than peripheral (i.e., muscle) protein synthesis and are converted to urea to a greater extent than are milk proteins. Alternatively, observed differences might be explained by differences in leucine content or absorption kinetics.

In the present study, the combined muscle thickness of the VI and VL increased in both the rice protein (0.2 cm) and whey protein (0.5 cm) conditions. Lean body mass increased in the rice protein condition by 2.5 kg, and it also increased in the whey protein condition by 3.2 kg. Combined bench press and leg press 1-RM strength increased in the rice protein condition by 76.4 kg and in the whey protein condition by 89.5 kg. However, no significant differences were observed between the two conditions for any measure.

Conclusion

The results suggest that differences in protein composition are of less relevance when protein is consumed in high doses throughout periodized RT. Rice protein isolate administration post resistance exercise decreases fat-mass and increases lean body mass, skeletal muscle hypertrophy, power and strength comparable to whey protein isolate. Rice protein isolate is an excellent plant protein alternative to animal protein to optimize the effects of resistance training.

Example 2

While digestibility of rice protein isolate (RPI) in rats has been shown to be inferior to animal protein (87% vs. 97% for casein), as shown above, administration of 48 grams of RPI following resistance exercise decreased fat-mass and increased lean body mass, skeletal muscle hypertrophy, power and strength comparable to whey protein isolate (WPI). This study sought to investigate the amino acid rate of appearance in the blood of 48 grams of RPI compared to 48 grams of WPI.

This study investigated the comparative appearance in the blood of total amino acids (TAA), non-essential amino acids (NEA) and essential amino acids (EEA) after the administration of RPI compared to WPI.

Methods

A double blind, two-period, two-sequence, crossover study was performed to assess the amino acid appearance in the blood after the administration of RPI and WPI from a fasted condition. The crossover design consisted of ten participants randomly assigned within each of the two sequences (AB, BA), indicating that every participant received the two protein supplements during the two periods separated by a one week washout period. Each protein supplement was administered in the same quantity of 48 grams of RPI (Growing Naturals Rice Protein Isolate made with Oryzatein® rice protein, Axiom Foods, Oro Valley, Ariz.) or WPI (Nutra Bio Whey Protein Isolate, Middlesex, N.J.) that was taken in a liquid formulation of 500 ml of water. The WPI and RPI supplements were matched to be isonitrogenous and isocaloric. The amino acid profile of each formulation was the same as in Example 1. The study protein that was given to the participants remained unknown to both the participants and the researchers for the entirety of the study.

Ten students currently enrolled at The University of Tampa volunteered for this study. The participants were 22.2±4.2 years of age, had an average bodyweight of 77.4±0.6 kg, and an average height of 176.8 cm±8.6 cm. All subjects did not have any physical or medical health complications according to past health examinations and further had to be a non-smoker to be included in this study. Participants were required to abstain from consuming any protein supplements for one month prior and during the wash-out of seven days. The volunteers had to complete an overnight fast for a duration of 12 hours before the morning of the study. This study was approved by the Institutional Review Board at The University of Tampa and each participant had signed an informed consent before being recruited into the study.

After a 12 hour overnight fast the 10 subjects were randomly assigned to receive either 48 grams of RPI (Growing Naturals Rice Protein Isolate (Chocolate Power) made with Oryzatein® rice protein, Axiom Foods, Oro Valley, Ariz. and having the amino acid profile shown in Table 2) or WPI (Nutra Bio Whey Protein Isolate (Dutch Chocolate), Middlesex, N.J., also shown in Table 2), in a double-blind, crossover design, separated by a washout phase of 7 days. Blood draws were taken immediately prior to, and at 1, 2, 3, and 4 hours following supplementation.

Measurement of Amino Acids

The amino acids measured in the blood plasma consisted of the nine essential amino acids (histidine, isoleucine, leucine, lysine, methionine, phenylalanine, tryptophan, threonine, and valine), as well as thirteen non-essential amino acids (alanine, arginine, asparagine, aspartic acid, citrulline, cystine, glutamic acid, glutamine, glycine, ornithine, proline, serine, and tyrosine). Amino acid concentrations were measured in the blood plasma prior to the oral administration of RPI or WPI to establish baseline measurements. All amino acid concentrations were then tested by taking blood plasma samples at 1 hour, 2 hours, 3 hours, and 4 hours following the consumption of one of the two protein supplements. The second period began after a seven day wash-out period and initial blood test was completed once again to reassess the concentration of each amino acid in the blood plasma prior to taking the protein that the subject had not already consumed. Measurement of amino acid plasma concentrations were then done consecutively in the same manner as the subsequent week in the pattern of 1 hour, 2 hours, 3 hours, and 4 hours. Chromatography measures the amount of active amino acids and metabolite in the blood plasma.

Data Analysis

The area under the concentration vs. time curve (AUC) was calculated using the linear trapezoidal rule from time zero until the last time point of sampling t (AUC0–t). Cmin and Cmax were defined as the minimum and maximum observed concentrations, respectively. tmax was the time at which Cmax was reached. AUC of the five conditions were compared and analyzed by paired-samples t-tests. A P-value<0.05 was considered statistically significant. Analyses were performed with the SPSS software package version 16.0 for Windows.

Results

WPI and RPI showed a significant difference for Tmax for essential amino acids (Table 4; EAA: RPI 87±7 min, WPI 67±4 min, p=0.03), non-essential amino acids (NEA: RPI 97±4 min, WPI 71±5 min, p<0.001), and total amino acids (TA: RPI 93±4 min, WPI 69±3 min, p<0.001), however no significant differences were detected for AUC (EAA: RPI 649.5±140.9 nmol/ml, WPI 754.2±170.0 nmol/ml, p=0.64; NEA: RPI 592.7±118.2 nmol/ml, WPI 592.7±121.2 nmol/ml, p=0.98; TA: RPI 615.9±88.6 nmol/ml, WPI 661.1±98.7 nmol/ml, p=0.74), and Cmax (EAA: RPI 176.1±37.5 nmol/ml, WPI 229.5±51.2 nmol/ml, p=0.41; NEA: RPI 160.0±31.1 nmol/ml, WPI 178.4±34.0 nmol/ml, p=0.69; TA: RPI 166.6±23.4 nmol/ml, WPI 199.3±28.8 nmol/ml, p=0.38). See FIGS. 3A-3C.

TABLE 4

Cumulative Bioavailability of Essential and Non-Essential Amino Acids. Data expressed as Geometric Mean ± SEM.

|  | Rice | Whey | P-Value |
| --- | --- | --- | --- |
| EAA | | | |
| AUC | 649.5 ± 140.9 | 754.2 ± 169.9 | 0.64 |
| $C_{max}$ | 176.1 ± 37.6 | 229.5 ± 51.2 | 0.41 |
| $T_{max}$ (min) | 87 ± 7 | 67 ± 4 | *0.03 |
| NEAA | | | |
| AUC | 592.7 ± 118.2 | 596.6 ± 121.2 | 0.98 |
| $C_{max}$ | 160.0 ± 31.1 | 178.4 ± 34.0 | 0.69 |
| $T_{max}$ | 97 ± 4 | 69 ± 3 | *0.00 |
| TAA | | | |
| AUC | 615.9 ± 88.6 | 661.1 ± 98.7 | 0.74 |
| $C_{max}$ | 166.6 ± 23.4 | 199.3 ± 28.8 | 0.39 |
| $T_{max}$ | 93 ± 4 | 69 ± 3 | *0.00 |

*Represents significance at an alpha of 0.05.

Figure 4A:
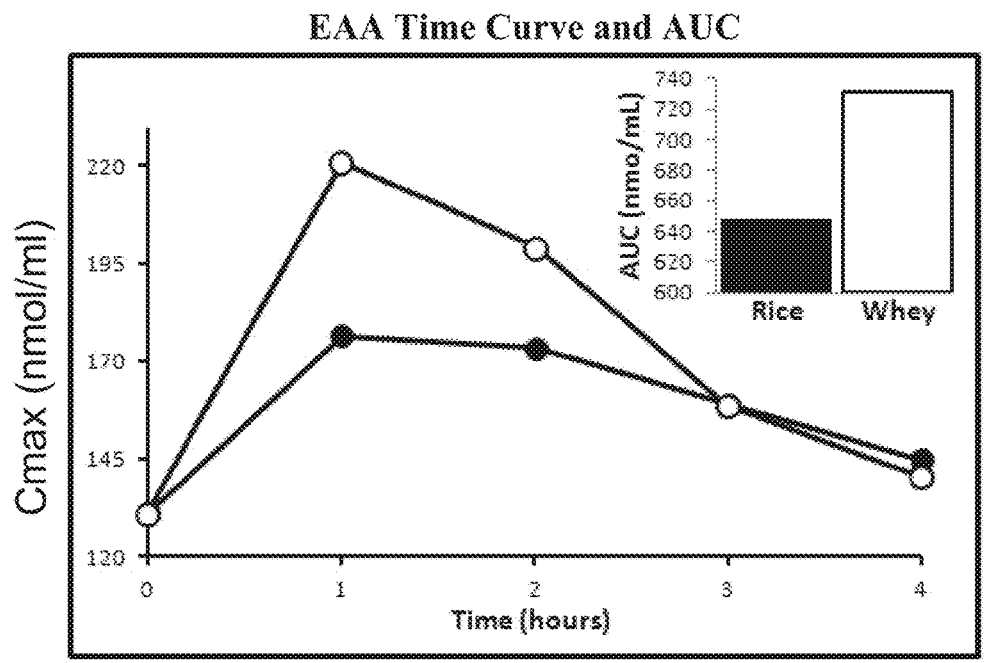
FIGS. 4A-4C depict blood levels of rice protein isolate versus whey protein isolate after ingestion.
Figure 4B:
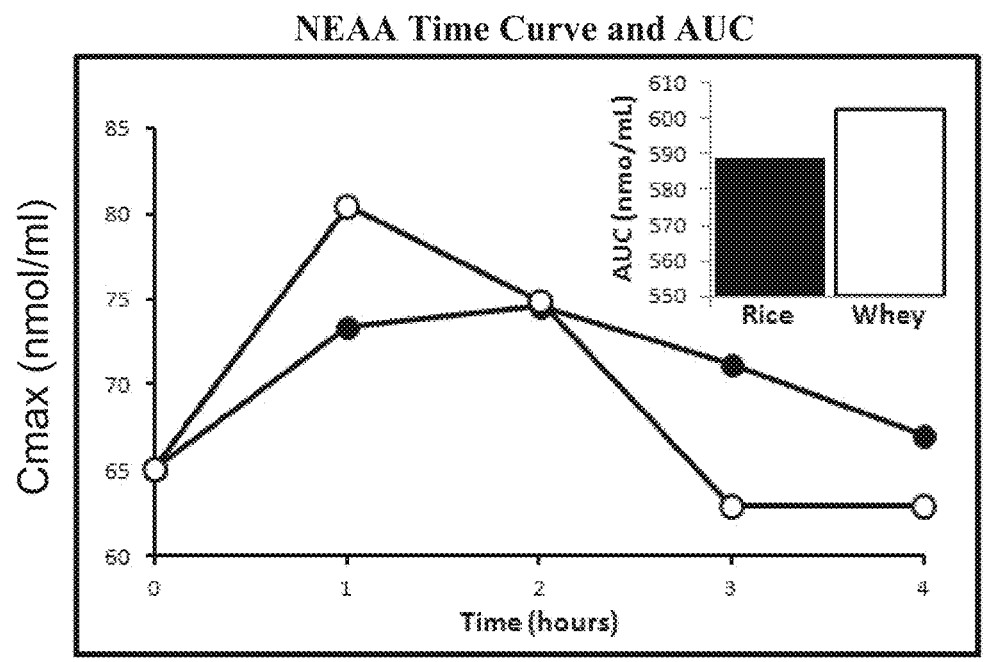
Figure 4C:
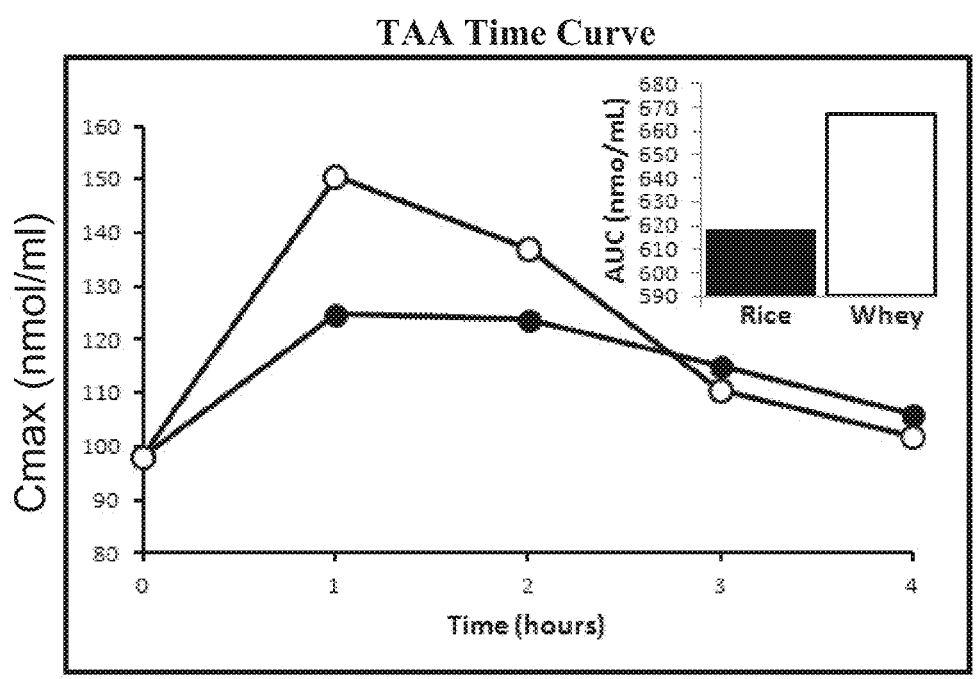

FIG. 4A shows the EAA Time Curve and AUC. FIG. 4B shows the NEAA curve and AUC. FIG. 4C shows the TAA Time Curve and AUC.

On an individual amino acid basis, WPI and RPI showed bioequivalency (0.80-1.25 of the geometric mean ratio (GMR)) for AUC and Cmax for all amino acids with the exception of cysteine, isoleucine, leucine, lysine, and threonine, in which WPI performed significantly better. Tmax differed between WPI and RPI for histidine, phenylalanine, threonine, asparagine, glutamic acid, glycine, ornithine, proline, and serine. The pharmacokinetic parameters of individual EAAs and NEAAs is shown in Table 5 and Table 6, respectively.

TABLE 5

| Amino Acid | RPI | WPI | LCL | UCL |
| --- | --- | --- | --- | --- |
| Histidine | | | | |
| AUC | 738.1 ± 37.2 | 683.9 ± 39.8 | 1.08 | 1.07 |
| $C_{max}$ | 191.6 ± 10.0 | 190.9 ± 7.2 | .98 | 1.01 |
| $T_{max}$ | 2.3 ± 0.2 | 0.9 ± 0.1 | 2.81 | 2.50 |
| Isoleucine | | | | |
| AUC | 317.5 ± 37.0 | 424.4 ± 31.5 | .71 | .77 |
| $C_{max}$ | 92.7 ± 11.7 | 144.0 ± 5.8 | .59 | .70 |
| $T_{max}$ | 1.2 ± 0.2 | 1.2 ± 0.0 | .83 | 1.08 |
| Leucine | | | | |
| AUC | 597.9 ± 38.5 | 769.9 ± 50.8 | .77 | .77 |
| $C_{max}$ | 167.2 ± 12.1 | 240.7 ± 12.8 | .68 | .70 |
| $T_{max}$ | 1.1 ± 0.0 | 1.4 ± 0.1 | .80 | .71 |
| Lysine | | | | |
| AUC | 1,367.4 ± 60.8 | 1,755.0 ± 101.5 | .79 | .76 |
| $C_{max}$ | 364.8 ± 19.7 | 533.6 ± 36.1 | .69 | .67 |
| $T_{max}$ | 1.1 ± 0.1 | 1.1 ± 0.1 | 1.00 | 1.10 |
| Methionine | | | | |
| AUC | 135.5 ± 11.9 | 163.7 ± 17.1 | .84 | .81 |
| $C_{max}$ | 38.8 ± 3.0 | 54.2 ± 6.8 | .75 | .68 |
| $T_{max}$ | 1.3 ± 0.1 | 1.1 ± 0.0 | 1.22 | 1.22 |
| Phenylalanine | | | | |
| AUC | 264.8 ± 11.9 | 226.6 ± 12.7 | 1.18 | 1.16 |
| $C_{max}$ | 71.3 ± 4.0 | 66.8 ± 3.7 | 1.06 | 1.07 |
| $T_{max}$ | 1.4 ± 0.2 | 0.8 ± 0.1 | 1.72 | 1.74 |

TABLE 5-continued

| Amino Acid | RPI | WPI | LCL | UCL |
|---|---|---|---|---|
| Tryptophan | | | | |
| AUC | 556.5 ± 40.9 | 659.8 ± 69.4 | .87 | .81 |
| $C_{max}$ | 152.0 ± 11.8 | 199.1 ± 23.2 | .79 | .73 |
| $T_{max}$ | 1.6 ± 0.1 | 1.3 ± 0.0 | 1.12 | 1.28 |
| Threonine | | | | |
| AUC | 609.7 ± 30.1 | 778.7 ± 53.5 | .79 | .76 |
| $C_{max}$ | 163.6 ± 9.1 | 236.9 ± 18.6 | .70 | .67 |
| $T_{max}$ | 1.6 ± 0.1 | 1.1 ± 0.0 | 1.42 | 1.60 |
| Valine | | | | |
| AUC | 1,257.7 ± 98.6 | 1,326.0 ± 69.8 | .92 | .97 |
| $C_{max}$ | 343.4 ± 29.9 | 399.2 ± 19.4 | .82 | .89 |
| $T_{max}$ | 1.6 ± 0.0 | 1.3 ± 0.1 | 1.24 | 1.18 |

TABLE 6

| Amino Acid | Rice Protein | Whey Protein | LCL | UCL |
|---|---|---|---|---|
| Alanine | | | | |
| AUC | 830.1 ± 68.5 | 850.0 ± 62.4 | .96 | .98 |
| $C_{max}$ | 223.8 ± 17.8 | 250.5 ± 15.4 | .87 | .90 |
| $T_{max}$ | 1.5 ± 0.2 | 1.3 ± 0.1 | 1.11 | 1.26 |
| Arginine | | | | |
| AUC | 636.9 ± 40.7 | 524.8 ± 43.2 | 1.23 | 1.19 |
| $C_{max}$ | 183.6 ± 14.7 | 168.4 ± 11.9 | 1.07 | 1.09 |
| $T_{max}$ | 1.3 ± 0.0 | 0.9 ± 0.0 | 1.36 | 1.37 |
| Asparagine | | | | |
| AUC | 606.5 ± 44.6 | 669.0 ± 55.7 | .91 | .89 |
| $C_{max}$ | 161.9 ± 14.4 | 199.7 ± 15.2 | .79 | .82 |
| $T_{max}$ | 1.9 ± 0.1 | 1.1 ± 0.1 | 1.88 | 1.67 |
| Aspartic Acid | | | | |
| AUC | 22.0 ± 4.1 | 24.6 ± 3.7 | .85 | .91 |
| $C_{max}$ | 6.2 ± 1.2 | 8.9 ± 1.7 | .69 | .70 |
| $T_{max}$ | 1.5 ± 0.3 | 1.3 ± 0.1 | 1.07 | 1.26 |
| Citrulline | | | | |
| AUC | 91.0 ± 12.2 | 98.8 ± 16.1 | .95 | .89 |
| $C_{max}$ | 26.0 ± 2.5 | 32.4 ± 6.2 | .89 | .73 |
| $T_{max}$ | 1.9 ± 0.1 | 1.9 ± 0.0 | .95 | .98 |
| Cystine | | | | |
| AUC | 90.5 ± 18.6 | 122.7 ± 19.5 | .69 | .76 |
| $C_{max}$ | 25.4 ± 5.3 | 40.1 ± 6.1 | .58 | .66 |
| $T_{max}$ | 1.4 ± 0.0 | 1.1 ± 0.1 | 1.33 | 1.2 |
| Glutamic Acid | | | | |
| AUC | 151.9 ± 19.4 | 182.3 ± 56.6 | .86 | .81 |
| $C_{max}$ | 44.2 ± 6.6 | 66.9 ± 6.6 | .62 | .69 |
| $T_{max}$ | 1.3 ± 0.4 | 0.9 ± 0.1 | 1.09 | 1.84 |
| Glutamine | | | | |
| AUC | 1,439.9 ± 52.3 | 1,484.2 ± 82.7 | .99 | .95 |
| $C_{max}$ | 373.2 ± 15.6 | 406.9 ± 21.5 | .92 | .90 |
| $T_{max}$ | 1.2 ± 0.3 | 1.0 ± 0.1 | .96 | 1.32 |
| Glycine | | | | |
| AUC | 833.3 ± 53.6 | 703.9 ± 39.8 | 1.17 | 1.19 |
| Cmax | 218.9 ± 11.4 | 201.8 ± 13.8 | 1.06 | 1.10 |
| $T_{max}$ | 1.8 ± 0.2 | 1.1 ± 0.5 | 2.57 | 2.54 |
| Ornithine | | | | |
| AUC | 622.7 ± 49.6 | 602.2 ± 49.7 | 1.04 | 1.03 |
| $C_{max}$ | 169.1 ± 18.5 | 180.4 ± 9.7 | .88 | .99 |
| $T_{max}$ | 1.8 ± 0.0 | 0.9 ± 0.0 | 2.14 | 2.00 |
| Proline | | | | |
| AUC | 1,159.5 ± 71.7 | 1,263.2 ± 70.1 | .91 | .92 |
| $C_{max}$ | 313.7 ± 19.0 | 374.8 ± 19.1 | .82 | .84 |
| $T_{max}$ | 1.7 ± 0.1 | 1.1 ± 0.0 | 1.54 | 1.65 |

TABLE 6-continued

| Amino Acid | Rice Protein | Whey Protein | LCL | UCL |
|---|---|---|---|---|
| Serine | | | | |
| AUC | 618.1 ± 43.4 | 642.6 ± 68.1 | 1.00 | .93 |
| $C_{max}$ | 167.6 ± 15.70 | 211.5 ± 19.3 | .79 | .79 |
| $T_{max}$ | 1.8 ± 0.11 | 1.4 ± 0.5 | 2.22 | 2.10 |
| Tyrosine | | | | |
| AUC | 603.2 ± 47.0 | 588.1 ± 58.0 | 1.04 | 1.00 |
| $C_{max}$ | 167.1 ± 13.2 | 176.9 ± 19.1 | .97 | .91 |
| $T_{max}$ | 1.7 ± 0.3 | 1.4 ± 0.1 | 1.17 | 1.42 |

Discussion

The primary findings from this investigation were that RPI is an intermediate absorbed protein compared to the fast absorbing WPI and that the RPI showed only a 6.8% lower total amino acid appearance in the blood compared to WPI.

Absorption Kinetics

Comparing different high quality proteins, the digestion rate of proteins influences protein turnover and how amino acids support protein synthesis. Recent evidence suggests that differences in the rate of absorption of different proteins can affect the amplitude and possibly duration of MPS and that this effect is possibly accentuated with resistance exercise. The fast absorbed whey protein increases mixed muscle protein fractional synthetic rate at rest and after resistance exercise to a greater extent when compared to the slow absorbed casein. Whereas faster absorption seems to favor MPS, slower absorption seems to favor the satiating effect of proteins supplementation. Slow absorbed casein showed a stronger satiating effect and subsequent reduced food intake compared to whey when consumed as a preload to a meal. While TAA for WPI reached its maximum concentration after 69±3 min, RPI was significantly slower (93±4 min). On an individual amino acid basis, WPI was faster or equal for all amino acids with the exception of leucine, which reached Cmax faster in the RPI group. While not being bound to any mechanism, these unique and surprising absorption kinetics might be an additional explanation why 8 weeks of high-dose WPI or RPI supplementation showed no difference between groups in improving body composition and exercise performance. The slower overall absorption kinetics makes RPI an interesting candidate for satiety.

AUC

The digestibility (87%) and biological value (51%) of RPI is inferior to WPI (100%, and 100% respectively). Considering the 13% difference in digestibility or 49% difference biological value significant differences in TAA levels were expected. However, RPI showed only a 6.8% lower TAA appearance in the blood based on AUC and the difference to WPI was not statistically significant. These surprisingly small, non-significant differences in AUC match the Example 1 finding that 8 weeks of high-dose WPI or RPI supplementation did not result in significant difference in body composition and exercise performance. Using low-dose supplementation strategies, the amount of RPI should be increased by the lower amount of leucine and the reduced absorption to match WPI for optimal MPS in combination with resistance exercise.

The cross-over design is the most fundamental study design since all subjects are given both treatments therefore eliminating inter-subject variability between subjects. There was no missing data from the attrition of participants throughout the study as each participant completed the crossover for both treatments. The intra-subject coefficient of variation for Cmax were 2.3%-6.2% (mean=4.4%) for the essential amino acids and 2.0%-10.0% (mean=5.9%) for the non-essential amino acids. The intra-subject coefficient of variations for AUC were 3.5%-7.3% (mean=4.9%) for the essential amino acids and 1.9-12.7% (mean=6.6%) for the non-essential amino acids. The low coefficient of variation concludes that there is greater than 90% power of determining bioequivalence.

For non-metabolizable supplemental nutrients, bioavailability is effectively equivalent to absorbability. Currently, there are no pre-specifications on the design and procedures of bioequivalence studies that involve endogenous compounds and active metabolites. The processes of absorption, distribution, metabolism, and elimination of rice and whey protein are accompanied by the endogenous production of non-essential amino acids and transamination of amino acids converting to other compounds at the same time. Other studies suggest that the rate of endogenous production of amino acids within the body remains unaffected directly by the levels accumulated in the body at that time, but the rate of production is alternately dependent upon the dietary composition of amino acids and the percentage fulfilled according to the daily nutritional guidelines.

Conclusion

These findings suggest that RPI, compared to WPI (fast) and casein (slow), is an intermediate digesting protein. While RPI showed a 6.8% lower total amino acid appearance in the blood based on AUC, the difference was not statistically significant. These findings suggest that RPI, compared to WPI (fast) and casein (slow), is an intermediate digesting protein. While RPI showed a 6.8% lower total amino acid appearance in the blood based on AUC, the difference was not statistically significant.

Example 3

Rice vs. Whey vs. Placebo Supplementation on Body Composition, Strength, and Muscle Thickness. Nine resistance trained male participants were selected for use in a study to determine differences between the exercise training results using a rice protein supplement, a whey protein supplement, or placebo. Three participants were selected for each group.

Each participant trained five times per week for four weeks using a hypertrophy and strength oriented periodized resistance training program. Each of the three participants in the whey protein group was given 18 g of whey protein concentrate (having 1.8 g of leucine total per 18 g serving) and each of the three participants in the rice protein group was given 18 g of rice protein concentrate (having 1.4 g leucine per 18 g serving).

Every workout session was monitored and post workout ingestion of protein was monitored by an investigator. On non-workout days protein supplementation was taken before bed time. Table 7 shows statistics gathered from the participants:

TABLE 7

|  | Age (yrs) | Weight (kg) | Height (cm) |
|---|---|---|---|
| Whey Protein Concentrate | 22.0 | 73.2 | 183.9 |
| Rice Protein Concentrate | 21.7 | 69.5 | 178.1 |
| Placebo | 21.1 | 68.0 | 177.3 |

After the study period lean body mass was measured using DEXA, muscle thickness was measured using ultrasound, and strength was measured using bench press and leg press.

Figure 5A:
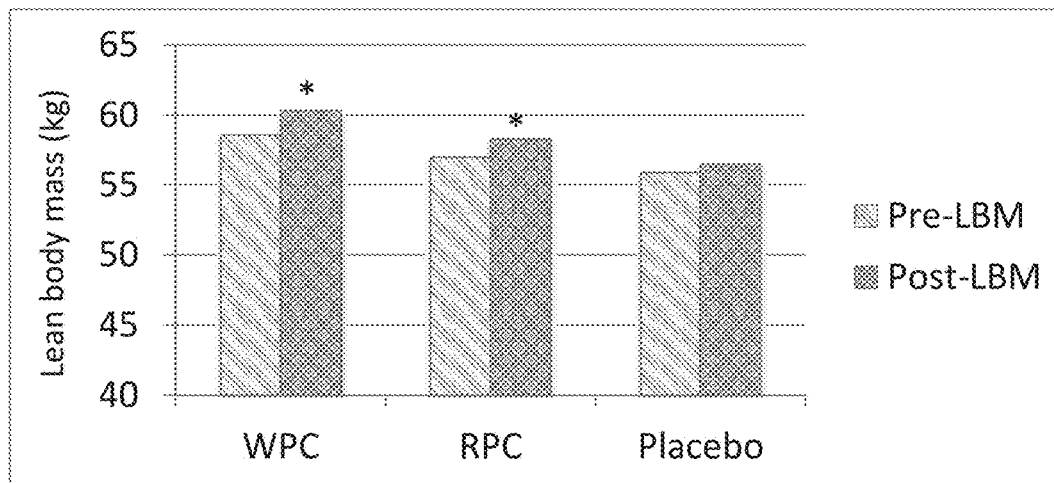
FIGS. 5A-5D depict test results for subjects using whey protein isolate, rice protein isolate, or placebo for supplementation after exercise training.

Table 8 displays the results for lean body mass (LBM) before and after the four week experimental period. FIG. 5A displays those same results graphically.

TABLE 8

|  | Pre-LBM (kg) | Post-LBM (kg) | Delta Change (kg) |
|---|---|---|---|
| Whey Protein Concentrate | 58.6 | 60.4 | 1.8 (+3%) |
| Rice Protein Concentrate | 57.0 | 58.5 | 1.5 (+3%) |
| Placebo | 55.9 | 56.5 | 0.6 (+1%) |

Figure 5B:
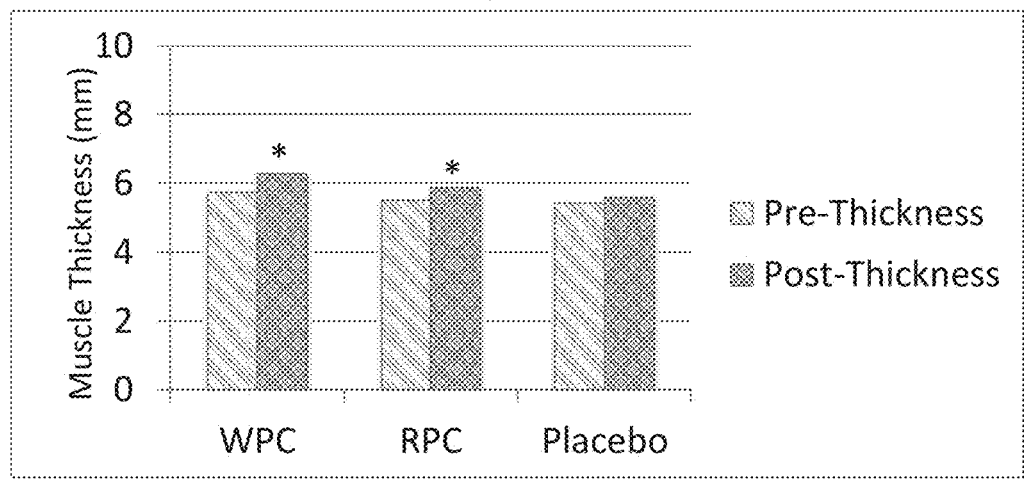

Table 9 displays the results for muscle thickness before and after the four week experimental period. FIG. 5B displays those same results graphically.

TABLE 9

|  | Pre-Thickness | Post-Thickness | Delta Change |
|---|---|---|---|
| Whey Protein Concentrate | 5.8 | 6.3 | 0.5 (+9%) |
| Rice Protein Concentrate | 5.5 | 5.9 | 0.4 (+7%) |
| Placebo | 5.4 | 5.6 | 0.2 (+4%) |

Figure 5C:
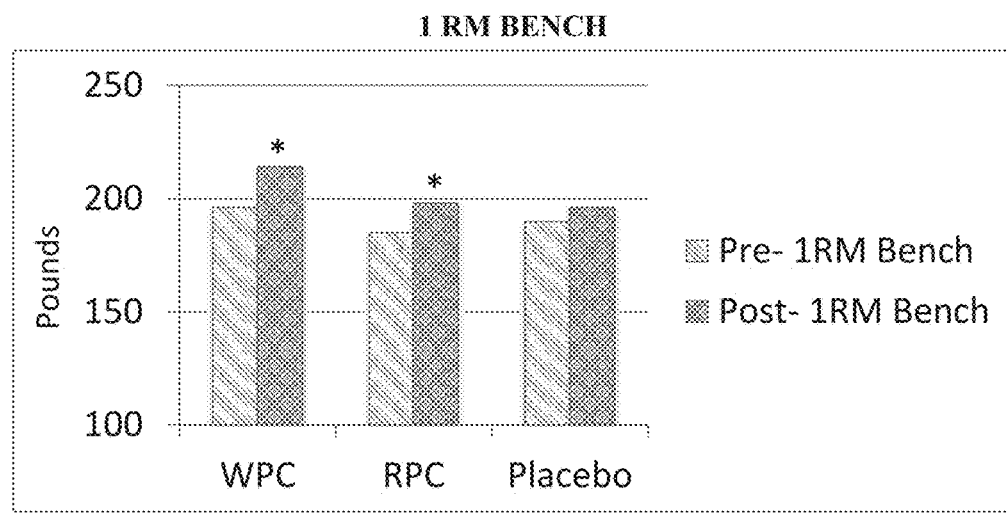

Table 10 displays the results for 1 rep max (RM) bench press before and after the four week experimental period. FIG. 5C displays those same results graphically.

TABLE 10

|  | Pre-1RM Bench | Post-1RM Bench | Delta Change |
|---|---|---|---|
| Whey Protein Concentrate | 196 | 214 | 18 (+9%) |
| Rice Protein Concentrate | 185 | 198 | 13 (+7%) |
| Placebo | 190 | 196 | 6 (+3%) |

Figure 5D:
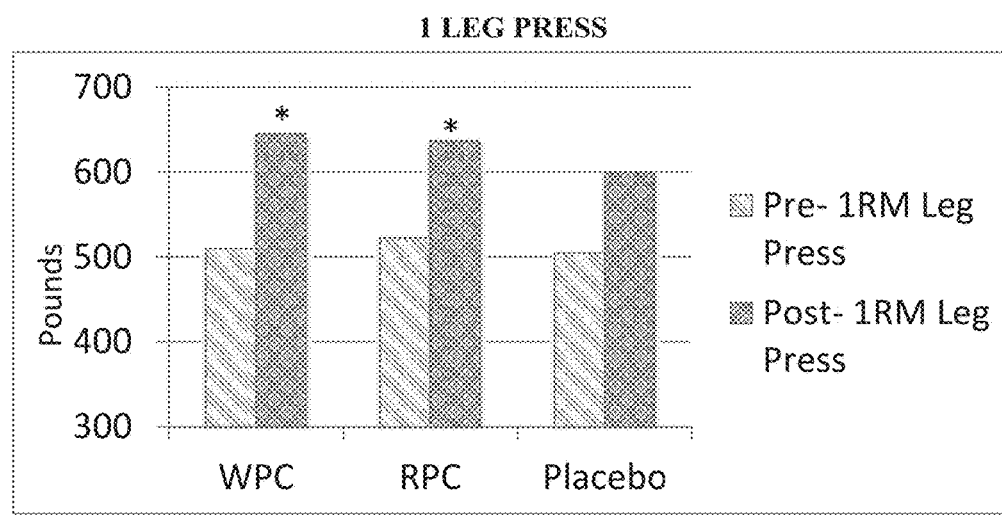

Table 11 displays the results for 1RM leg press before and after the four week experimental period. FIG. 5D displays those same results graphically.

TABLE 11

|  | Pre-1RM Leg Press | Post-1RM Leg Press | Delta Change |
|---|---|---|---|
| Whey Protein Concentrate | 510 | 645 | 135 (+26%) |
| Rice Protein Concentrate | 523 | 637 | 114 (+22%) |
| Placebo | 505 | 600 | 95 (+19%) |

This study showed that an 18 gram dose of whey protein concentrate or rice protein concentrate significantly increase LBM, muscle thickness and leg and upper body strength during after 4 weeks of resistance training. The suboptimal leucine levels from rice protein concentrate (less than the optimum 1.7-3.5 g range) surprisingly showed no significant difference from the optimal leucine levels from whey protein concentrate in LBM muscle thickness and increase leg and upper body strength.

Example 4

The purpose of the following study is to use a well-controlled animal model to test whether rice protein concentrate (RPC, Axiom Foods) is able to stimulate anabolic skeletal muscle signaling pathways relative to whey protein concentrate (WPC) and soy protein concentrate (SPC) feedings.

Study Protocol

Male Wistar rats (~225-250 g; Harlan Laboratories) were used for this study. Table 12 outlines rats in each group:

TABLE 12

|  | Whey Protein Concentrate (WPC) | Soy Protein Concentrate (SPC) | Rice Protein Concentrate (RPC) |
| --- | --- | --- | --- |
| Mid-Dose (~19 g human eq.) | 3 | 3 | 3 |
| Low Dose (~10 g human eq.) | 3 | 3 | 3 |

The night prior to gavage feeding, rats were fasted overnight (a total of 15-18 hours). The day of feeding, rats were gavage-fed the respective test protein in 1-2 ml of water under light isoflurane anesthesia. The human-equivalent dosing paradigms were established per the methods of Reagan-Shaw et al.

After gavage feedings, rats recovered for 60 min in their home cages. They were then injected with a metabolic tracer for muscle protein synthesis (i.p. injection of 5.44 g puromycin dihydrochloride in 1 ml of sterile PBS). Following injections, rats recovered for an additional 30 min in their home cages (90 min total after gavage-feeding).

90 minutes following gavage feeding (30 min after puromycin-tracer injections), rats were euthanized using CO2 narcosis. Hind limb mixed gastrocnemius muscles were extracted and processed for Western blotting and muscle protein synthesis, respectively.

Results

Markers of Muscle Protein Synthesis

Figure 6:
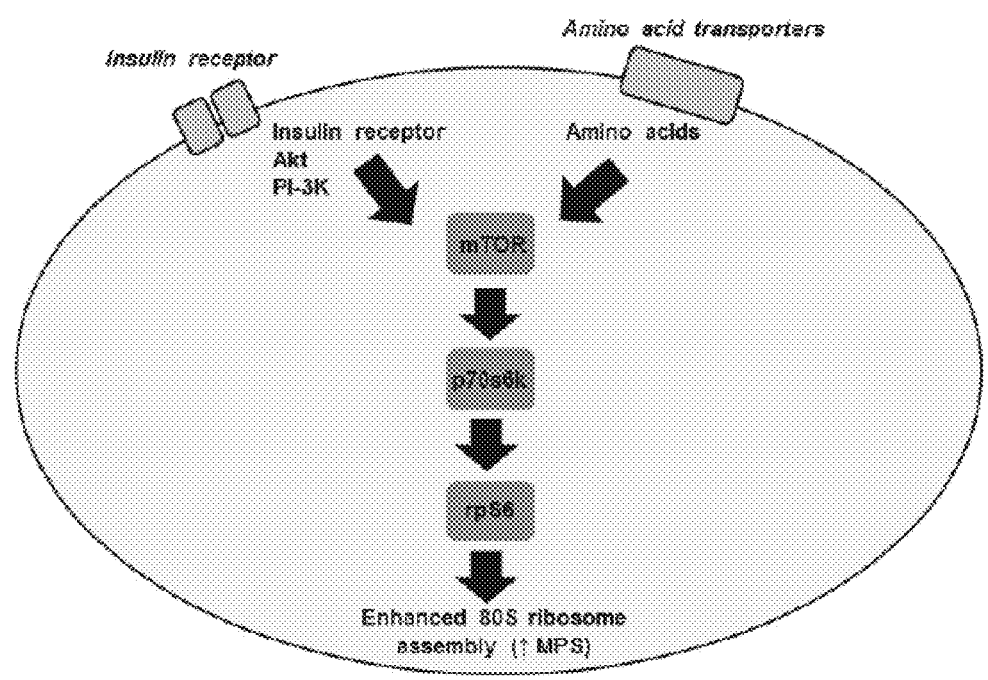
FIG. 6 depicts a diagram of the mTORC1 pathway.

A diagram of the mTORC1 pathway is provided in FIG. 6.

Anabolic Protein Signaling (Akt-mTOR Pathway).

Figure 7:
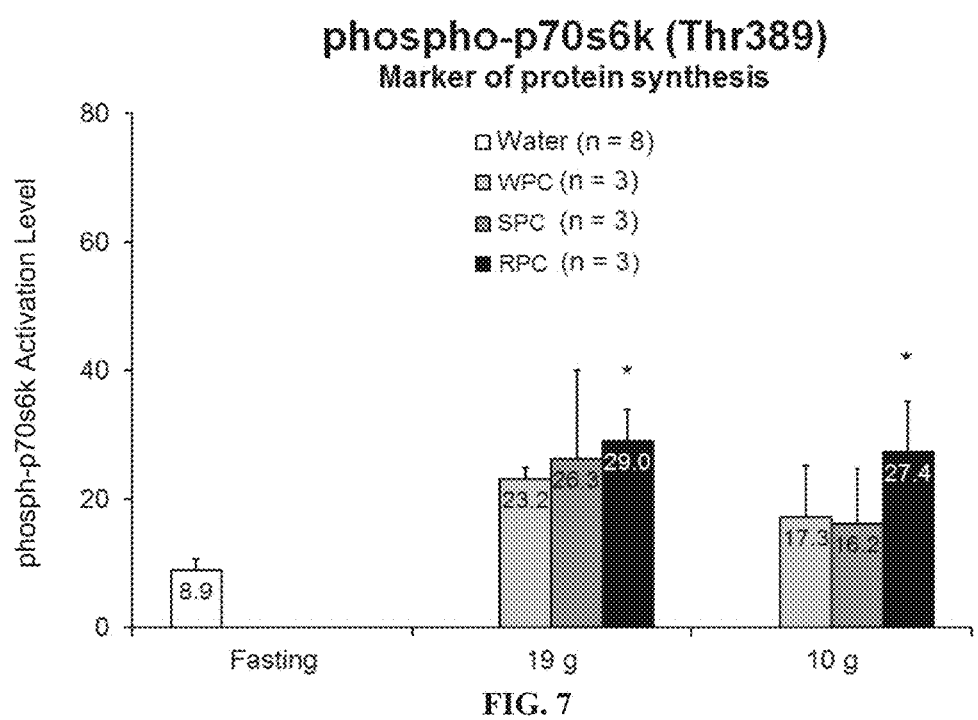
FIG. 7 depicts results for phosph-p70s6k (Thr389) activation using whey protein isolate, soy protein isolate and rice protein isolate.

At the human equivalent dose (HED) of 19 g and 10 g, RPC significantly activated phosph-p70s6k (Thr389) signaling in comparison to control (water), while WPC and SPC failed to reach significance (see FIG. 7; phosph-p70s6k (Thr389) activation by WPC, SPC and RPC). RPC showed a 29% greater activation than WPC and a 14% greater activation than SPC at a HED of 19 g. At a lower dose, a HED of 10 g, the differences became even greater: RPC activated this marker of protein synthesis by 58% over WPC and even 69% over SPC.

Example 5

A 6 week premature, female newborn who is unable to digest breast milk and animal-derived formula is given a formula comprising a rice protein isolate as the only protein source. The rice formula has less than about 90 mg leucine per gram rice protein isolate and less than about 50 mg lysine per gram rice protein isolate. One to five ounces of the rice formula are given to the newborn every two to four hours. The newborn gains weight at a comparable rate to newborns ingesting breast milk or animal-derived formula.

Example 6

A colicky two month old baby who has been ingesting breast milk and animal-derived formula is switched to a baby formula comprising rice protein isolate as the only protein source and water. The baby is given one to eight ounces of the baby formula every two to four hours. The baby's colick subsides and the baby gains weight at a comparable rate to babies ingesting breast milk or animal-derived formula.

Example 7

A 25 year old male marathon runner begins a regimen of ingesting a 31 gram serving of Growing Naturals Rice Protein Isolate after running or engaging in weight training. The marathon runner reports sustained muscle and strength growth after four weeks of using the supplement. Testing shows that the runner's VO2 max has increased 3% over the same period. The runner reports increased endurance on training runs. The runner reports that his recovery is faster since starting the rice protein regimen. He notes that he is able to run greater distances on consecutive days without tiring. He is able to run at higher volume with greater speed after starting the rice protein regimen. He reports that he is also able to recover from weight training sessions faster. For instance, he is able to weight train on consecutive days with greater strength and volume than prior to starting the rice protein regimen. The runner also reports that when he ingests the rice protein isolate after a run or after weight training, his body has less muscle soreness than before he started the rice protein regimen.

Example 8

A 35 year old male body builder ingests a 31 gram serving of Growing Naturals Rice Protein Isolate during weight training sessions for eight weeks. The body builder reports sustained muscle and strength growth with decreased fat after the eight week period. The body builder's weight remains about the same over the eight week period. He reports that since using the rice protein isolate, he has less muscle soreness.

Example 9

A 49 year old female cancer patient is unable to maintain her weight during chemotherapy. She has a loss of appetite and nausea upon ingesting solid foods or animal-derived protein products. She begins ingesting three 31 gram servings of Growing Naturals Rice Protein Isolate each day. Her appetite improves and the rate of her weight loss decreases.

Example 10

A 75 year old male is unable to maintain his weight and has steady weight decreases over the period of a year. He begins ingesting a 60 gram serving of Growing Naturals Rice Protein Isolate each day, along with continuing on his regular diet. After an 8 week period, the male has gained several pounds and has improved energy.

What is claimed is:
1. A method for improving a result of exercise training in a subject, the method comprising:
   administering to the subject a nutritional supplement comprising a protein;

wherein the protein of the nutritional supplement consists of a rice protein isolate comprising about 80 mg of leucine per gram of protein in the rice protein isolate and about 31 mg of lysine per gram of protein in the rice protein isolate;

wherein ingestion of a 48 gram dose of the rice protein isolate by the subject following each session of an 8 week periodized training protocol results in at least one of decreased fat-mass, increased lean body mass, increased skeletal muscle hypertrophy, increased power output, and increased strength.

2. The method of claim 1, wherein the rice protein isolate further comprises about 41 mg of isoleucine per gram of protein in the rice protein isolate and about 58 mg of valine per gram of protein in the rice protein isolate.

3. The method of claim 1, wherein the nutritional supplement further comprises about 41 mg of isoleucine per gram of protein in the rice protein isolate.

4. The method of claim 1, wherein the nutritional supplement further comprises about 58 mg of valine per gram of protein in the rice protein isolate.

5. The method of claim 1, wherein the rice protein isolate comprises about 54 mg alanine, about 77 mg arginine, about 87 mg aspartic acid, about 21 mg cysteine, about 174 mg glutamic acid, about 43 mg glycine, about 22 mg histidine, about 41 mg isoleucine, about 28 mg methionine, about 53 mg phenylalanine, about 45 mg proline, about 49 mg serine, about 35 mg threonine, about 14 mg tryptophan, about 47 mg tyrosine, and about 58 mg valine per gram of protein in the rice protein isolate.

6. The method of claim 1, wherein the rice protein isolate is a brown rice protein isolate.

7. A method of supplementing the diet of a subject, comprising:

administering to the subject a nutritional supplement comprising a rice protein isolate;

wherein all of the protein of the nutritional supplement is from the rice protein isolate;

wherein the nutritional supplement comprises about 80 mg of leucine per gram of protein in the rice protein isolate; and wherein ingestion of a 48 gram dose of the rice protein isolate by the subject following exercise results in at least one of decreased fat-mass, increased lean body mass, increased skeletal muscle hypertrophy, increased power output, and increased strength.

8. The method of claim 7, wherein the nutritional supplement further comprises about 41 mg of isoleucine per gram of protein in the rice protein isolate.

9. The method of claim 7, wherein the nutritional supplement further comprises about 58 mg of valine per gram of protein in the rice protein isolate.

10. The method of claim 7, wherein the rice protein isolate comprises about 54 mg alanine, about 77 mg arginine, about 87 mg aspartic acid, about 21 mg cysteine, about 174 mg glutamic acid, about 43 mg glycine, about 22 mg histidine, about 41 mg isoleucine, about 31 mg lysine, about 28 mg methionine, about 53 mg phenylalanine, about 45 mg proline, about 49 mg serine, about 35 mg threonine, about 14 mg tryptophan, about 47 mg tyrosine, and about 58 mg valine per gram of protein in the rice protein isolate.

11. The method of claim 7, wherein the rice protein isolate is a brown rice protein isolate.

* * * * *